US007176158B2

(12) United States Patent
Chow et al.

(10) Patent No.: US 7,176,158 B2
(45) Date of Patent: Feb. 13, 2007

(54) POLYMERIZATION CATALYST COMPOSITION

(75) Inventors: Stanley Wai-Yan Chow, Sugarland, TX (US); Guo-Xin Jin, Shanghai (CN); Zerong Lin, Kingwood, TX (US); Robert J. Wittenbrink, Kingwood, TX (US); Dao Zhang, Changchun (CN)

(73) Assignee: ExxonMobil Chemical Patents Inc., Houston, TX (US)

( * ) Notice: Subject to any disclaimer, the term of this patent is extended or adjusted under 35 U.S.C. 154(b) by 215 days.

(21) Appl. No.: 10/693,424

(22) Filed: Oct. 24, 2003

(65) Prior Publication Data

US 2004/0147771 A1 Jul. 29, 2004

Related U.S. Application Data

(60) Provisional application No. 60/446,607, filed on Feb. 12, 2003, provisional application No. 60/435,228, filed on Dec. 20, 2002, provisional application No. 60/435,046, filed on Dec. 20, 2002, provisional application No. 60/434,913, filed on Dec. 20, 2002, provisional application No. 60/434,082, filed on Dec. 17, 2002, provisional application No. 60/433,934, filed on Dec. 17, 2002, provisional application No. 60/421,282, filed on Oct. 25, 2002, provisional application No. 60/421,164, filed on Oct. 25, 2002, provisional application No. 60/421,163, filed on Oct. 25, 2002.

(51) Int. Cl.
*B01J 31/00* (2006.01)
*B01J 37/00* (2006.01)
*C08F 4/44* (2006.01)
*C08F 4/02* (2006.01)
*C08F 4/60* (2006.01)

(52) U.S. Cl. .............. 502/159; 502/102; 502/117; 502/155; 502/165; 502/166; 502/167; 502/200; 502/207; 526/134; 526/161

(58) Field of Classification Search ............ 502/159, 502/160, 162, 167, 102, 117, 155, 165, 166, 502/200, 207; 526/134, 161
See application file for complete search history.

(56) References Cited

U.S. PATENT DOCUMENTS

| | | | |
|---|---|---|---|
| 3,670,043 A | 6/1972 | Kubicek et al. | 260/683 D |
| 4,343,935 A | 8/1982 | Laidler et al. | 542/414 |
| 4,590,288 A | 5/1986 | Klemann | 556/112 |
| 4,800,224 A | 1/1989 | Kaschig | 546/12 |
| 4,871,705 A | 10/1989 | Hoel | 502/117 |
| 4,891,412 A | 1/1990 | Kaschig | 526/265 |
| 4,954,592 A | 9/1990 | Kaschig | 526/265 |
| 4,983,739 A | 1/1991 | Kaschig | 546/268 |
| 5,336,795 A | 8/1994 | Lisowsky | 556/56 |
| 5,393,903 A | 2/1995 | Gratzel et al. | 556/137 |
| 5,504,232 A | 4/1996 | Winter et al. | 556/7 |
| 5,543,373 A | 8/1996 | Winter et al. | 502/103 |
| 5,629,254 A | 5/1997 | Fukuoka et al. | 502/117 |
| 5,631,391 A | 5/1997 | Canich | 556/11 |
| 5,641,871 A | 6/1997 | Rohde et al. | 534/15 |
| 5,654,454 A | 8/1997 | Peifer et al. | 556/11 |
| 5,679,816 A | 10/1997 | Timmers et al. | 556/53 |
| 5,696,045 A | 12/1997 | Winter et al. | 502/113 |
| 5,714,425 A | 2/1998 | Chabrand et al. | 502/117 |
| 5,714,427 A | 2/1998 | Winter et al. | 502/117 |
| 5,739,366 A | 4/1998 | Imuta et al. | 556/11 |
| 5,741,868 A | 4/1998 | Winter et al. | 526/127 |
| 5,763,542 A | 6/1998 | Winter et al. | 526/127 |
| 5,831,106 A | 11/1998 | Langhauser et al. | 512/11 |
| 5,847,176 A | 12/1998 | Sullivan | 556/11 |
| RE36,103 E | 2/1999 | Winter et al. | 526/160 |
| 5,880,056 A | 3/1999 | Tsutsui et al. | 502/103 |
| 5,892,077 A | 4/1999 | Resconi et al. | 556/11 |
| 6,103,946 A | 8/2000 | Brookhart, III et al. | 585/523 |
| 6,107,501 A | 8/2000 | Shamshoum et al. | 556/11 |
| 6,133,387 A | 10/2000 | Xu et al. | 526/172 |
| 6,143,911 A | 11/2000 | Fujita et al. | 556/11 |
| 6,150,482 A | 11/2000 | Brookhart et al. | 526/161 |
| 6,150,544 A | 11/2000 | Seki et al. | 556/27 |
| 6,153,549 A | 11/2000 | Hubscher et al. | 502/103 |
| 6,191,294 B1 | 2/2001 | Resconi et al. | 556/11 |
| 6,218,558 B1 | 4/2001 | Kato et al. | 556/12 |
| 6,232,484 B1 | 5/2001 | Schaverien et al. | 556/53 |
| RE37,208 E | 6/2001 | Winter et al. | 526/348 |
| 6,268,518 B1 | 7/2001 | Resconi et al. | 556/43 |
| RE37,384 E | 9/2001 | Winter et al. | 502/117 |
| 6,306,791 B1 | 10/2001 | Schaverien et al. | 502/117 |
| 6,319,874 B1 | 11/2001 | Winter et al. | 502/152 |
| RE37,573 E | 3/2002 | Winter et al. | 556/7 |
| 6,352,953 B1 | 3/2002 | Seki et al. | 502/103 |
| 6,365,690 B1 | 4/2002 | Lenges | 526/172 |
| 6,369,254 B1 | 4/2002 | Resconi et al. | 556/11 |
| 6,800,774 B1 * | 10/2004 | Li et al. | 556/33 |

(Continued)

FOREIGN PATENT DOCUMENTS

CN 1257875 A 6/2000

(Continued)

OTHER PUBLICATIONS

Abstract, EP0496193 B1, (published Jul. 29, 1992).

(Continued)

*Primary Examiner*—J. A. Lorengo
*Assistant Examiner*—J. Pasterczyk

(57) ABSTRACT

Copolymerization of Ni(H) or Co(II) acenaphthene diimine complexes containing olefinic substituents on aryl groups in the presence of a free radical initiator results in polymerized late transition metal catalysts which can be used for olefin polymerization or oligomerization. These catalysts have high catalyst activity for olefin polymerization or oligomerization.

17 Claims, No Drawings

U.S. PATENT DOCUMENTS

| | | | |
|---|---|---|---|
| 6,841,693 B1 * | 1/2005 | Watanabe et al. | 556/32 |
| 2002/0082162 A1 | 6/2002 | Li et al. | 502/167 |

FOREIGN PATENT DOCUMENTS

| | | |
|---|---|---|
| CN | 1294137 A | 5/2001 |
| CN | 1352204 A | 6/2001 |
| CN | 1306012 A | 8/2001 |
| CN | 1306013 A | 8/2001 |
| CN | 1328879 A | 1/2002 |
| CN | 1352203 A | 6/2002 |
| CN | 1371923 A | 10/2002 |
| CN | 1371924 A | 10/2002 |
| EP | 0 426 646 A1 | 5/1989 |
| EP | 0 496 193 A1 | 7/1992 |
| WO | WO 01 92342 A2 | 12/2001 |

OTHER PUBLICATIONS

Gasperini et al, "Synthesis of Ar-BIAN Ligands (Ar-BIAN=Bis(aryl)acenaphthenequinonediimine) Having Strong Electron-Withdrawing Substituents on the Aryl Rings and Their Relative Coordination Strength toward Palladium(0) and -(II) Complexes", Organometallics 2002, 21, pp. 2950-2957.

Abstract—Liu, Chang-Kun et al., "Allyl-containing Iron Post-metallocene Catalyst for Ethylene Polymerization", Changchun Institute of Applied Chemistry, Chinese Academy of Science, Changchun, 130022, Peoples Republic of China, Gaodeng Xuexiao Huaxue Xuebao (2001), 22(7), pp. 1233-1236, and translation of article in Chinese.

Liu, Changkun et al., "Polymer-incorporated Iron Catalysts for Ethylene Polymerization—A View Approach to Immobilize Iron Olefin Catalysts on Polystyrene Chains", New Journal of Chemistry (2002), 26(10), pp. 1485-1489, XP008017403.

Liu, Changkun et al., "Preparation of Post-metallocene Macromolecular Catalyst for Olefin Polymerization", retrieved from STN Database accession No. 137:33685 XP002241590 (Chemical Abstracts Service, Columbus, Ohio); Changchun Institute of Applied Chemistry, Chinese Academy of Sciences, Peoples Republic of China (STN Abstract).

Jin, Guoxin et al., "Preparation of Unsymmetric Post-metallocene Macromolecular Catalysts for Olefin Polymerization", retrieved from STN Database accession No. 137:33686 XP002241591 (Chemical Abstracts Service, Columbus, Ohio); Changchun Institute of Applied Chemistry, Chinese Academy of Sciences, Peoples Republic of China.

Liu, Chang-Kun et al., "Polymerized Unsymmetrical Iron Post-Metallocene Catalyst for Ethylene Polymerization" retrieved from STN Database accession No. 136:325871 XP002241592, (Chemical Abstracts Service, Columbus, Ohio); Changchun Institute of Applied Chemistry, Chinese Academy of Sciences, Peoples Republic of China.

Jin Guoxin, et al., "Non-metallocene" olefin polymerization catalyst, Chinese Journal of Applied Chemistry, vol. 16, No. 1, Feb. 1999.

Shen Haoyu, et al., New Type Late Transition Metal Catalysts for Olefin Polymerization—Nickel-based Olefin Polymerization Catalyst, Progress in Chemistry, Jan. 2003, pp. 60-66.

* cited by examiner

POLYMERIZATION CATALYST COMPOSITION

STATEMENT OF RELATED APPLICATIONS

This application claims priority from U.S. Ser. No. 60/446,607 filed Feb. 12, 2003. This application is related to U.S. Ser. No. 60/421,282 filed Oct. 25, 2002; U.S. Ser. No. 60/421,163 filed Oct. 25, 2002; U.S. Ser. No. 60/421,164 filed Oct. 25, 2002; U.S. Ser. No. 60/433,934 filed Dec. 17, 2002; U.S. Ser. No. 60/434,082, filed Dec. 17, 2002; U.S. Ser. No. 60/434,913 filed Dec. 20, 2002; U.S. Ser. No. 60/435,228 filed Dec. 20, 2002; and U.S. Ser. No. 60/435,046 filed Dec. 20, 2002.

FIELD OF THE INVENTION

This invention relates to methods of polymerizing or oligomerizing one or more olefins using one or more activators with one or more polymerized catalyst compounds prepared by polymerizing one or more free radical polymerizable monomers (such as styrene) with one or more different olefin polymerization catalyst precursor compounds containing terminal unsaturation.

BACKGROUND

U.S. Pat. No. 5,714,425 describes metallocene catalyst compositions having a polymerizable olefinic group. These metallocenes are described as being useful to prepare polyolefins. In addition, these metallocenes are described as being polymerized with one or more alpha-olefins so that the metallocene is copolymerized with the alpha-olefin. This composition is then described as useful to polymerize olefins. But U.S. Pat. No. 5,714,425 does not disclose free-radical polymerization of catalyst compositions having a polymerizable olefinic group with monomers such as styrene, isobutylene, 1,3-butadiene and the like.

U.S. Pat. No. 5,679,816 discloses biscyclopentadienyl transition-metal complexes containing a conjugated diene ligand group.

U.S. Pat. No. 6,150,544 and U.S. Pat. No. 6,352,953 disclose bimetallic, metallacyclic catalyst compounds where one metal is a Group-4 metal and the other metal is a Group-3 metal. (Likewise, it is also known in the art to prepolymerize a heterogeneous catalyst system in the presence of at least one olefin see EPA 426,646 and U.S. Pat. No. 4,871,705.)

SUMMARY

This invention relates to a composition comprising the product of combining, in the presence of a free radical initiator, one or more monomers that can be polymerized by a free radical initiator and a catalyst precursor compound represented by the formula:

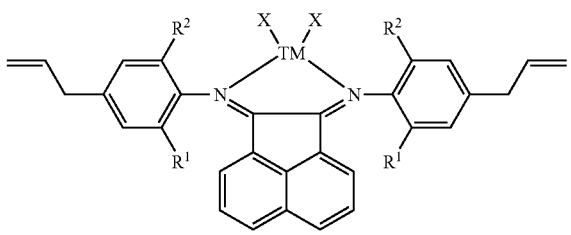

wherein each X is independently a hydrocarbyl group or a halogen, and TM is any Group-4-11 metal, any Group-9-11 metal, or Ni or Co. $R^1$ and $R^2$ are independently hydrogen or hydrocarbyl groups.

This invention also relates to the above complex copolymerized with other molecules provided that the polymerization method is free-radical initiable. This invention also relates to methods to polymerize olefins using the above compositions.

DETAILED DESCRIPTION

Definitions

The term "hydrocarbyl radical" is sometimes used interchangeably with "hydrocarbyl" throughout this document. For purposes of this disclosure, "hydrocarbyl radical" encompasses $C_1$–$C_{200}$ radicals. These radicals can be linear, branched, or cyclic, and when cyclic, aromatic or non-aromatic. Thus, the term "hydrocarbyl radical", in addition to unsubstituted hydrocarbyl radicals, encompasses substituted hydrocarbyl radicals, halocarbyl radicals, and substituted halocarbyl radicals, as these terms are defined below.

Substituted hydrocarbyl radicals are radicals in which at least one hydrogen atom has been replaced with a functional group such as $NR''_2$, $OR''$, $PR''_2$, $SR''$, $BR''_2$, $SiR''_3$, $GeR''_3$ and the like or where at least one non-hydrocarbon atom or group has been inserted within the hydrocarbyl radical, such as O, S, $NR''$, $PR''$, $BR''$, $SiR''_2$, $GeR''_2$, and the like, where R" is independently a $C_1$–$C_{30}$ hydrocarbyl or halocarbyl radical.

Halocarbyl radicals are radicals in which one or more hydrocarbyl hydrogen atoms have been substituted with at least one halogen or halogen-containing group (e.g. F, Cl, Br, I).

Substituted halocarbyl radicals are radicals in which at least one hydrocarbyl hydrogen or halogen atom has been substituted with a functional group such as $NR''_2$, $OR''$, $PR''_2$, $SR''$, $BR''_2$, $SiR''_3$, $GeR''_3$ and the like or where at least one non-carbon atom or group has been inserted within the halocarbyl radical such as O, S, $NR''$, $PR''$, $BR''$, $SiR''_2$, $GeR''_2$, and the like where R" is independently a $C_1$–$C_{30}$ hydrocarbyl or halocarbyl radical provided that at least one halogen atom remains on the original halocarbyl radical.

In some embodiments, a hydrocarbyl radical is independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomers. The radical may then be subjected to the types of substitutions described above. Also, terms like "propyl" and "hexyl" encompass all isomers, e.g. propyl means both n-propyl and isopropyl; hexyl includes all six carbon isomers including cyclic isomers.

Ancillary ligands serve to enforce the geometry around the metal center.

An "abstractable ligand" is a ligand that can be abstracted from the metal center by a cocatalyst leaving behind an activated catalyst.

For purposes of this disclosure oligomers have about 2–75 mer units. A mer is defined as a unit of an oligomer or polymer that originally corresponded to the monomer that was used in the polymerization reaction. For example, the mer of polyethylene would be ethylene.

In some structures throughout this specification, drawing the ligand-metal connection with an arrow, showing that the electrons for the bond originally came from the ligand, sometimes indicates coordination. At other times, drawing a solid line, showing the bond's covalent nature, indicates coordination. One of ordinary skill in the art recognizes that these depictions are interchangeable.

The term "alkyl" or "alkyl radical" refer to branched or unbranched, saturated or unsaturated, acyclic hydrocarbyl radical. Suitable alkyl radicals include, for example, methyl, ethyl, n-propyl, i-propyl, 2-propenyl (or allyl), vinyl, n-butyl, t-butyl, i-butyl (or 2-methylpropyl). In particular embodiments, alkyls are $C_{1-200}$ hydrocarbyls, $C_{1-50}$ hydrocarbyls, or $C_{1-20}$ hydrocarbyls.

Description

The inventive polymerized late transition metal catalyst precursors are prepared by copolymerizing transition metal acenaphtheno complexes with an olefin such as styrene in the presence of a radical initiator (e.g., AIBN). These olefins are sometimes referred to in this document as catalyst polymerization monomers because they copolymerize with the catalyst precursor. These complexes contain aryl groups that are substituted with polymerizable olefinic substituents. Divinyl benzene is optionally added to the copolymerization reaction medium to promote cross-linking.

Before polymerization into a polystyrene particle, the late transition metal catalyst precursors are sometimes simply called catalyst precursors. After polymerization, the catalyst precursors are sometimes called polymerized catalyst precursors. After activation, the polymerized catalyst precursors are sometimes called polymerized catalysts.

Inventive transition metal complexes with olefinically substituted aryl groups are synthesized. Then they are free-radical copolymerized with a simpler olefin. The resulting copolymer has units of polyolefin interspersed with enchained catalyst molecules (catalyst precursors).

In the presence of an activator, these enchained late transition metal complexes (catalyst precursors) function as ethylene or α-olefin polymerization or oligomerization catalysts. Ethylene or α-olefin monomers are sometimes referred to in this documents as olefin polymerization monomer because they represent the monomer or monomers that become polyolefins when invention catalysts are activated for olefin polymerization (as opposed to when invention catalysts are subjected to free-radical initiation). As shown in the Example section, aryl substituents other than the olefinic substituent sometimes affect catalyst performance.

Inventive late transition metal complexes are useful to prepare catalysts for olefin polymerization or oligomerization. More than one catalyst precursor compound may be copolymerized with the monomers in varying ratios.

Catalyst Compounds

The following formula represents catalyst compounds that are useful in this invention.

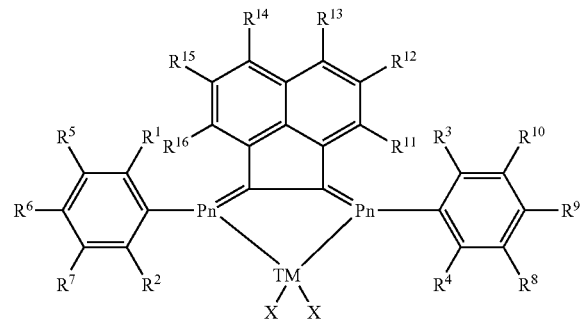

$R^1$–$R^{16}$ are hydrogen or hydrocarbyl radicals provided that at least one $R^5$–$R^{10}$ or $R^{11}$–$R^{16}$ is capable of polymerization by a free-radical-initiated polymerization reaction. TM represents a Group-4-11 transition metal. X represents an abstractable ligand. And Pn represents a Group-15 element.

Specific utile compounds include those represented by the formulas:

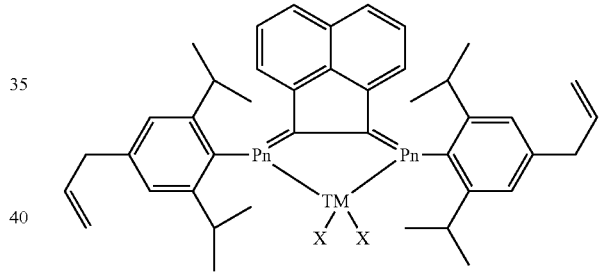

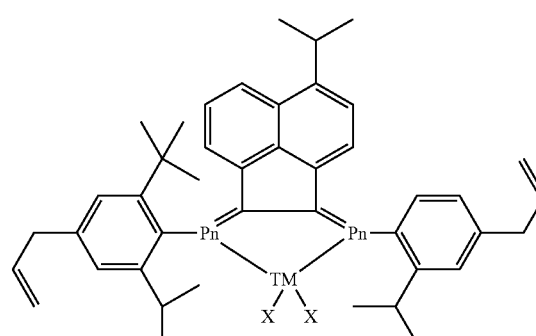

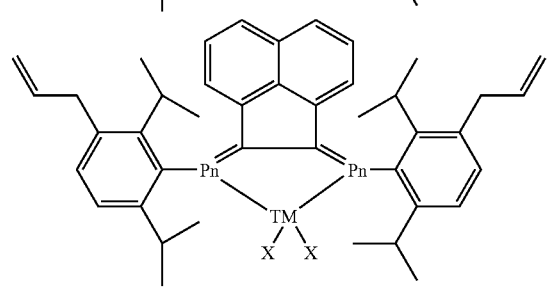

-continued
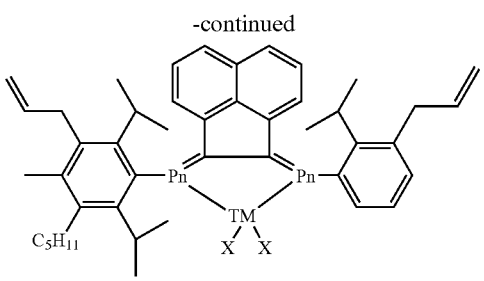
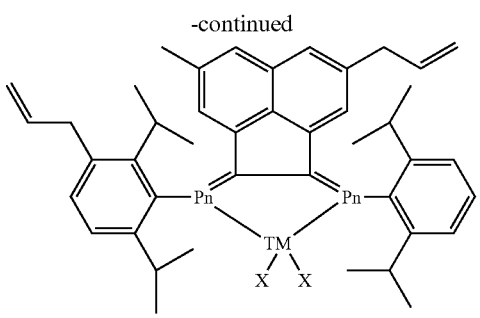
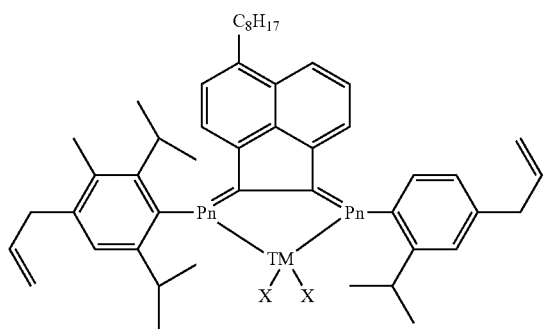
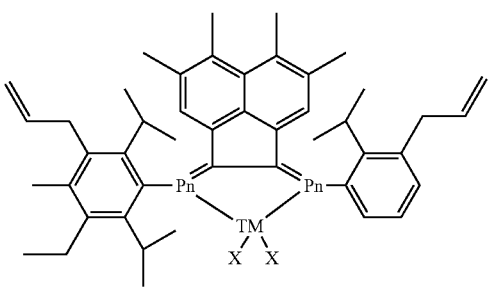
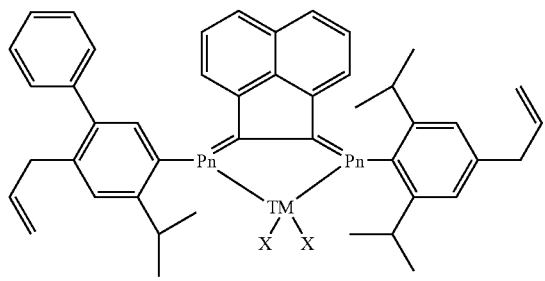
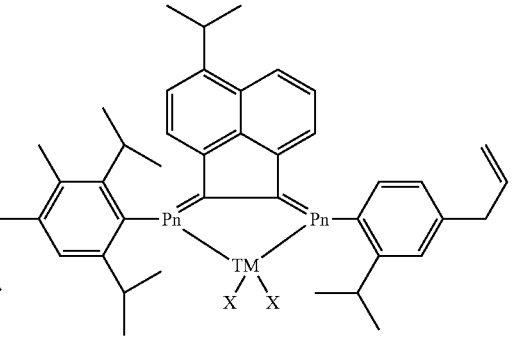
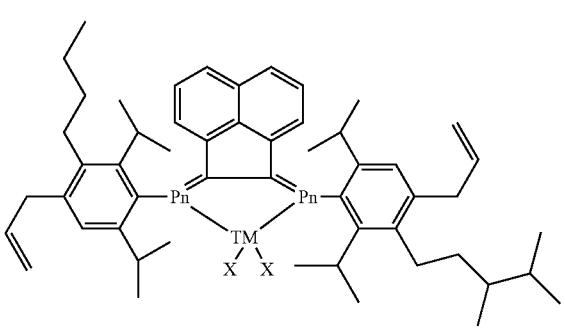
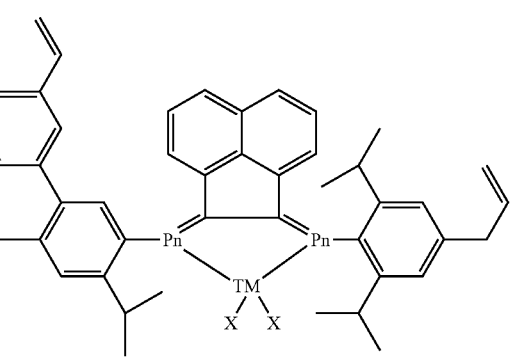
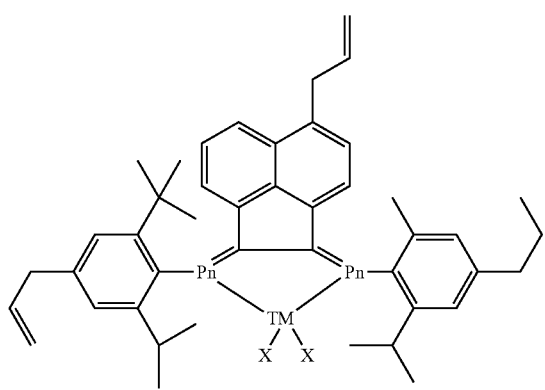
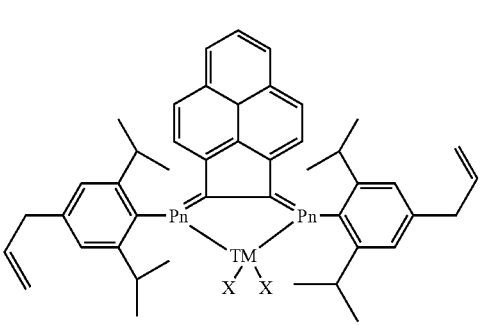

-continued

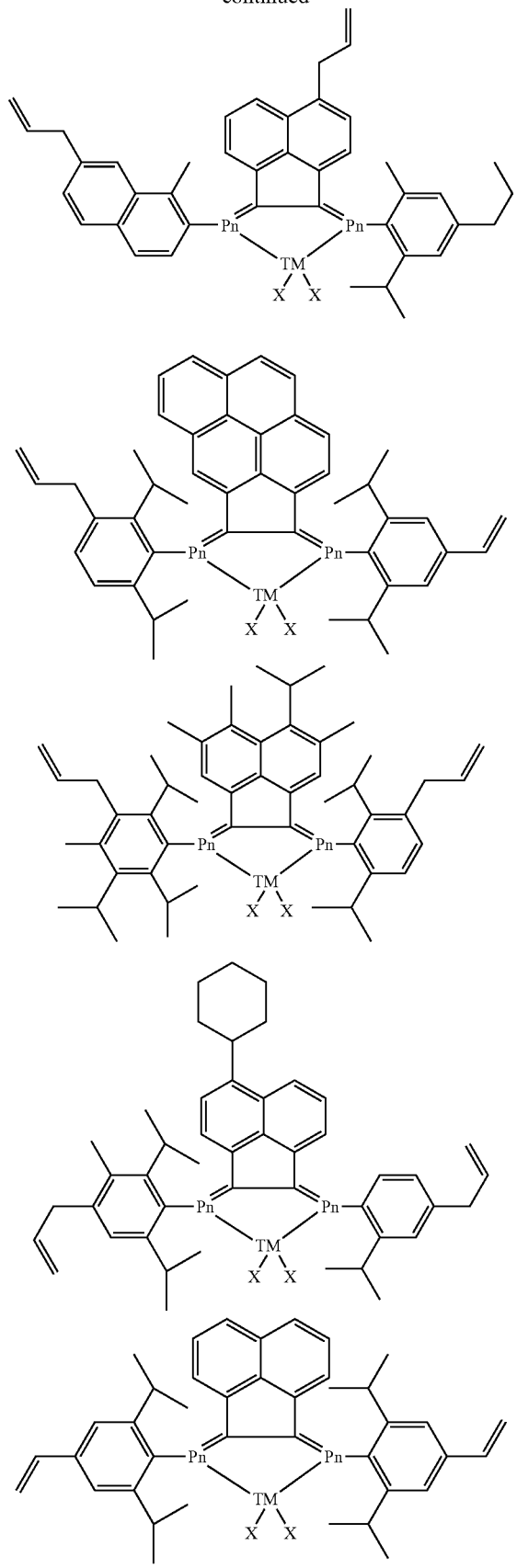

wherein each X is independently a hydrocarbyl group or a halogen, preferably a halogen, preferably bromine or chlorine; and M is any Group-4-11 metal, Group-9-11, or Co or Ni. Pn is a Group-15 element; preferably nitrogen.

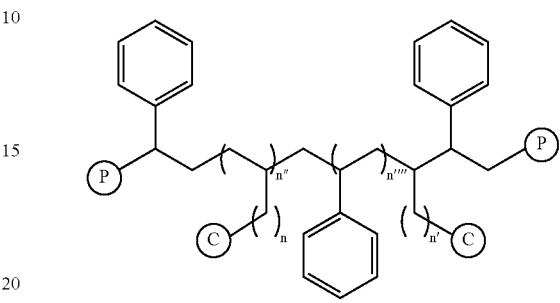

The above picture represents a schematic formula of the polymerized catalyst after polymerization. The P-labeled circles represent the bulk polyolefin/catalyst copolymer. The C-labeled circles represent the catalyst.

This section provides examples of how the ligands and complexes, as they exist before free-radical-initiated polymerization, are named and how the naming convention arises.

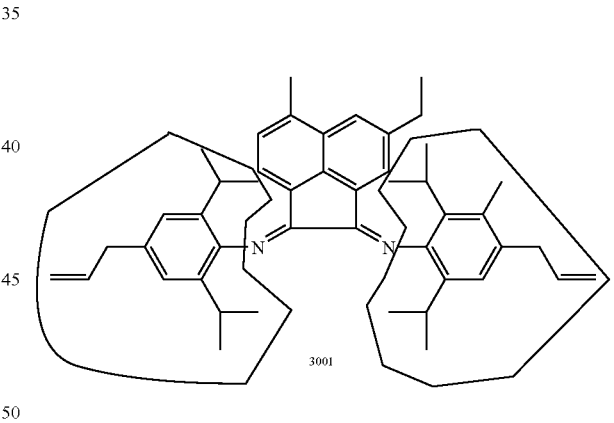

The ligand pictured above is called 1-(2,6-diisopropyl-4-allylphenylimino)-2-(2,6-diisopropyl-3-methyl-4-allylphenylimino)-4-ethyl-6-methylacenaphthene. As is readily apparent, the ligand is a disubstituted acenaphthene molecule. In this case, it is substituted at the 4-position with an ethyl radical. It is also substituted at the 6-position with a methyl radical. And the 1 and 2 positions are substituted with substituted imino groups. The substitutions on the imino groups are circled in the picture. These circled moieties are substituted phenyl radicals with isopropyl substitutions at their 2 and 6 positions and an allyl substitution at their 4-positions. Additionally, the right-hand-side phenyl radical is also substituted at its 3-position with a methyl group.

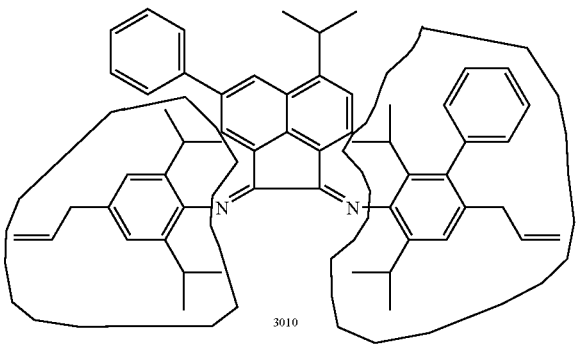

Similarly, the ligand pictured above is called 1-(2,6-diisopropyl-4-allylphenylimino)-2-(2,6-diisopropyl-3-phenyl-4-allylphenylimino)-5-isopropyl-7-phenylacenaphthene. As is readily apparent, the ligand is a disubstituted acenaphthene molecule. In this case, it is substituted at the 5-position with an isopropyl radical. It is also substituted at the 7-position with a phenyl radical. And the 1 and 2 positions are substituted with substituted imino groups, as in the first ligand picture. The substitutions on the imino groups are circled in the picture. These circled moieties are substituted phenyl radicals with isopropyl substitutions at their 2 and 6 positions and an allyl substitution at their 4-positions. Additionally, the right-hand-side phenyl radical is also substituted at its 3-position with a phenyl group.

The ligand is bidentate and can coordinate to an acceptor through the nitrogen atoms. For invention catalysts, the acceptor is a transition metal. To indicate that the substituted acenaphthene ligand is chelating, the acenaphthene name receives a suffix, -o, yielding acenaphtheno.

When the ligand above chelates or coordinates to a transition metal such as Ni, the complete name for the complex is [1-(2,6-diisopropyl-4-allylphenylimino)-2-(2,6-diisopropyl-3-phenyl-4-allylphenylimino)-5-isopropyl-7-phenylacenaphtheno-N,N'] dibromo nickel (II). The "N,N'" designation indicates that the ligand connects through its nitrogen atoms. Note that the transition metal has a set of charged bromide ligands; one or both of these act as the abstractactable ligand or leaving group. Thus, during olefin polymerization reactions with these complexes, either as shown or after their copolymerization with a styrenic monomer, one or both of these leaving groups are removed by the olefin polymerization activator. The formula for the complex appears below.

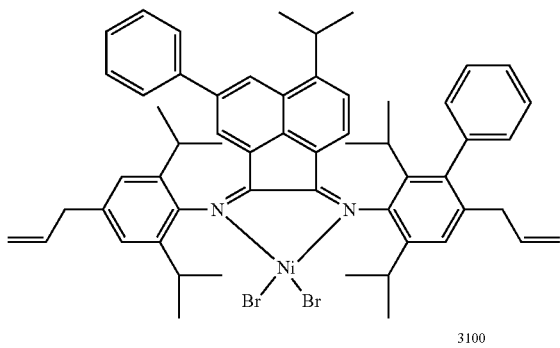

Useful Catalyst Compounds Include:
[1,2-bis(2,6-diheptyl-4-allyl-phenylimino)-6-hexylacenaphtheno-N,N']iodo pentyl nickel (II); [1,2-bis(2,6-diphenyl-4-allyl-phenylimino)-7-tetradecylacenaphtheno-N,N']dihexyl nickel (II); [1,2-bis(2,6-dipropyl-4-allyl-phenylimino)acenaphtheno-N,N']hexyl hydrido nickel (II); [1,2-bis(2,6-dipropyl-4-allyl-phenylimino)-4-butylacenaphtheno-N,N']methyl methoxy nickel (II); [1,2-bis(2,6-dipropyl-4-allyl-phenylimino)-3-methylacenaphtheno-N,N']ethyl butyl nickel (II); [1,2-bis(2,6-dibutyl-4-allyl-phenylimino)-5-phenylacenaphtheno-N,N']dimethoxy nickel (II); [1,2-bis(2,6-dioctyl-4-allyl-phenylimino)acenaphtheno-N,N']chloro butyl nickel (II); [1,2-bis(2,6-dipropyl-4-allyl-phenylimino)acenaphtheno-N,N']chloro octyl nickel (II); [1,2-bis(2,6-diethyl-4-allyl-phenylimino)-5-phenylacenaphtheno-N,N'] methoxy butyl nickel (II); [1,2-bis(2,6-dipropyl-4-allyl-phenylimino)-3-tetradecyl-6-ethylacenaphtheno-N,N'] methoxy chloro nickel (II); [1,2-bis(2,6-dipropyl-4-allyl-phenylimino)-6-phenylacenaphtheno-N,N']methyl pentyl nickel (II); [1,2-bis(2,6-diethyl-4-allyl-phenylimino)-7-phenylacenaphtheno-N,N']methoxy methyl nickel (II); [1,2-bis(2,6-dipropyl-4-allyl-phenylimino)acenaphtheno-N,N'] methoxy propyl nickel (II); [1,2-bis(2,6-diphenyl-4-allyl-phenylimino)-5-phenyl-3-ethylacenaphtheno-N,N']chloro methoxy nickel (II); [1,2-bis(2,6-dipropyl-4-allyl-phenylimino)-5-methyl-7-phenylacenaphtheno-N,N']hexyl ethoxy nickel (II); [1,2-bis(2,6-dimethyl-4-allyl-phenylimino)acenaphtheno-N,N']methoxy bromo nickel (II); [1,2-bis(2,6-dihexyl-4-allyl-phenylimino)-4-ethylacenaphtheno-N,N']hydrido chloro nickel (II); [1,2-bis(2,6-diheptadecyl-4-allyl-phenylimino)-8-decylacenaphtheno-N,N']octyl hydrido nickel (II); [1,2-bis(2,6-dimethyl-4-allyl-phenylimino)-3-ethylacenaphtheno-N,N']pentyl triphenylphosphine nickel (II); [1,2-bis(2,6-diphenyl-4-allyl-phenylimino)-5-phenyl-3-ethylacenaphtheno-N,N']butyl hydrido nickel (II); [1,2-bis(2,6-dihexyl-4-allyl-phenylimino)-4-octylacenaphtheno-N,N']chloro methoxy nickel (II); [1,2-bis(2,6-dimethyl-4-allyl-phenylimino)acenaphtheno-N,N']dihexyl nickel (II); [1,2-bis(2,6-dipropyl-4-allyl-phenylimino)acenaphtheno-N,N']butyl pentyl nickel (II); [1,2-bis(2,6-dipropyl-4-allyl-phenylimino)-3-ethyl-6-phenylacenaphtheno-N,N']propyl ethoxy nickel (II); [1,2-bis(2,6-diphenyl-4-allyl-phenylimino)-5-phenylacenaphtheno-N,N']methyl iodo nickel (II); [1,2-bis(2,6-dipentyl-4-allyl-phenylimino)-8-phenylacenaphtheno-N,N'] octyl iodo nickel (II); [1,2-bis(2,6-dioctyl-4-allyl-phenylimino)acenaphtheno-N,N']methoxy ethyl nickel (II); [1,2-bis(2,6-dihexyl-4-allyl-phenylimino)-7-phenylacenaphtheno-N,N']chloro pentyl nickel (II); [1,2-bis(2,6-diphenyl-4-allyl-phenylimino)-6-phenylacenaphtheno-N,N']octyl ethoxy nickel (II); [1,2-bis(2,6-dimethyl-4-allyl-phenylimino)acenaphtheno-N,N']pentyl hexyl nickel (II); [1,2-bis(2,6-dipropyl-4-allyl-phenylimino)-5-phenylacenaphtheno-N,N']heptyl methyl nickel (II); [1,2-bis(2,6-dimethyl-4-allyl-phenylimino)-8-propylacenaphtheno-N,N']propyl pentyl nickel (II); [1,2-bis(2,6-dimethyl-4-allyl-phenylimino)-4-phenylacenaphtheno-N,N']hexyl pentyl nickel (II); [1,2-bis(2,6-dipropyl-4-allyl-phenylimino)-6-hexyl-7-nonylacenaphtheno-N,N']dimethyl nickel (II); [1,2-bis(2,6-dipropyl-4-allyl-phenylimino)-6-methylacenaphtheno-N,N']methyl bromo nickel (II); [1,2-bis(2,6-dipropyl-4-allyl-phenylimino)acenaphtheno-N,N']methyl pentyl nickel (II); [1,2-bis(2,6-diphenyl-4-allyl-phenylimino)-6-phenylacenaphtheno-N,N']hexyl octyl nickel (II); [1,2-bis (2,6-dioctyl-4-allyl-phenylimino)-6-phenylacenaphtheno-N,N']hydrido heptyl nickel (II); [1,2-bis(2,6-diphenyl-4-allyl-phenylimino)acenaphtheno-N,N']methyl hexyl nickel (II); [1,2-bis(2,6-diethyl-4-allyl-phenylimino)-8-methylacenaphtheno-N,N']ethoxy bromo nickel (II); [1,2-bis(2,6-diphenyl-4-allyl-phenylimino)acenaphtheno-N,N']pentyl hydrido nickel (II); [1,2-bis(2,6-dihexadecyl-4-allyl-phenylimino)-7-nonadecylacenaphtheno-N,N']iodo chloro nickel (II); [1,2-bis(2,6-dipropyl-4-allyl-phenylimino)-3-phenyl-8-propylacenaphtheno-N,N']pentyl butyl nickel (II); [1,2-bis(2,6-diethyl-4-allyl-phenylimino)-5-propylacenaphtheno-N,N']chloro hexyl nickel (II); [1,2-bis(2,6-dihexyl-4-allyl-phenylimino)-7-nonadecylacenaphtheno-N,N']octyl ethyl nickel (II); [1,2-bis(2,6-diethyl-4-allyl-phenylimino)acenaphtheno-N,N']chloro iodo iridium (II); [1,2-bis(2,6-dioctyl-4-allyl-phenylimino)-8-phenylacenaphtheno-N,N'] bromo propyl iridium (II); [1,2-bis(2,6-dipropyl-4-allyl-phenylimino)acenaphtheno-N,N']hexyl hydrido iridium (II); [1,2-bis(2,6-dipropyl-4-allyl-phenylimino)-7-ethylacenaphtheno-N,N']chloro bromo copper (II); [1,2-bis(2,6-dipropyl-4-allyl-phenylimino)acenaphtheno-N,N']octyl bromo cobalt (II); [1,2-bis(2,6-diphenyl-4-allyl-phenylimino)-8-methylacenaphtheno-N,N']methyl hexyl cobalt (II); [1,2-bis(2,6-dihexyl-4-allyl-phenylimino)acenaphtheno-N,N']heptyl butyl cobalt (II); [1,2-bis(2,6-dipropyl-4-allyl-phenylimino)-7-phenylacenaphtheno-N,N']hydrido propyl nickel (II); [1,2-bis(2,6-dipropyl-4-allyl-phenylimino)-3-dodecylacenaphtheno-N,N']methoxy ethoxy nickel (II); [1,2-bis(2,6-diphenyl-4-allyl-phenylimino)acenaphtheno-N,N']bromo heptyl rhodium (II); [1,2-bis(2,6-dibutyl-4-allyl-phenylimino)-6,4-diphenylacenaphtheno-N,N']hexyl butyl rhodium (II); [1,2-bis(2,6-dipropyl-4-allyl-phenylimino)-8-hexadecyl-4-ethylacenaphtheno-N,N']ethoxy hydrido platinum (II); [1,2-bis(2,6-dipropyl-4-allyl-phenylimino)acenaphtheno-N,N']chloro bromo platinum (II); [1,2-bis(2,6-dipropyl-4-allyl-phenylimino)acenaphtheno-N,N']heptyl methoxy platinum (II); [1,2-bis(2,6-diphenyl-4-allyl-phenylimino)-7-hexylacenaphtheno-N,N']bromo ethyl palladium (II); [1,2-bis(2,6-dipropyl-4-allyl-phenylimino)-8-phenylacenaphtheno-N,N']hexyl octyl palladium (II); [1,2-bis(2,6-dipropyl-4-allyl-phenylimino)-7-phenylacenaphtheno-N,N']octyl ethyl palladium (II); [1,2-bis(2,6-dipropyl-4-allyl-phenylimino)-7-methyl-8-octylacenaphtheno-N,N']pentyl chloro palladium (II); [1,2-bis(2,6-ditetradecyl-4-allyl-phenylimino)-7-hexylacenaphtheno-N,N']bromo propyl palladium (II); [1,2-bis(2,6-dipropyl-4-allyl-phenylimino)acenaphtheno-N,N'] octyl chloro palladium (II); [1,2-bis(2,6-dihexyl-4-allyl-phenylimino)-6-hexylacenaphtheno-N,N']octyl bromo palladium (II); [1,2-bis(2,6-dihexyl-4-allyl-phenylimino)-7-octylacenaphtheno-N,N']methoxy iodo palladium (II); [1,2-bis(2,6-diphenyl-4-allyl-phenylimino)acenaphtheno-N,N'] pentyl propyl palladium (II); [1,2-bis(2,6-dihexyl-4-allyl-phenylimino)-6,7-diphenylacenaphtheno-N,N']pentyl triphenylphosphine nickel (II); [1,2-bis(2,6-dioctyl-4-allyl-phenylimino)acenaphtheno-N,N']ethoxy octyl nickel (II).

[1-(2,6-diethyl-4-allylphenyimino)-2-(2,6-diphenyl-4-allylphenyimino)-5-phenyl-8-pentadecylacenaphtheno-N,N'] dipropyl nickel (II); [1-(2,6-dihexyl-4-allylphenyimino)-2-(2,6-dinonyl-4-allylphenyimino)-7-methylacenaphtheno-N,N']iodo octyl nickel (II); [1-(2,6-dipropyl-4-allylphenyimino)-2-(2,6-diphenyl-4-allylphenyimino)-4-hexylacenaphtheno-N,N']hexyl butyl nickel (II); [1-(2,6-diphenyl-4-allylphenyimino)-2-(2,6-dipropyl-4-allylphenyimino)-6-ethyl-3-phenylacenaphtheno-N,N']iodo ethyl nickel (II); [1-(2,6-diethyl-4-allylphenyimino)-2-(2,6-dipentyl-4-allylphenyimino)-7-phenylacenaphtheno-N,N'] hexyl butyl nickel (II); [1-(2,6-dipropyl-4-allylphenyimino)-2-(2,6-diphenyl-4-allylphenyimino)-5-hexyl-8-phenylacenaphtheno-N,N']methoxy methyl nickel (II); [1-(2,6-dimethyl-4-allylphenyimino)-2-(2,6-diethyl-4-allylphenyimino)-3-phenylacenaphtheno-N,N']dipentyl nickel (II); [1-(2,6-diphenyl-4-allylphenyimino)-2-(2,6-diethyl-4-allylphenyimino)acenaphtheno-N,N']pentyl methoxy nickel (II); [1-(2,6-diheptadecyl-4-allylphenyimino)-2-(2,6-diphenyl-4-allylphenyimino)-3-phenyl-7-methylacenaphtheno-N,N']hexyl ethoxy nickel (II); [1-(2,6-dipropyl-4-allylphenyimino)-2-(2,6-dimethyl-4-allylphenyimino)-4-phenylacenaphtheno-N,N']methoxy chloro nickel (II); [1-(2,6-dipropyl-4-allylphenyimino)-2-(2,6-diethyl-4-allylphenyimino)-3-phenyl-5-propylacenaphtheno-N,N']ethyl propyl nickel (II); [1-(2,6-diphenyl-4-allylphenyimino)-2-(2,6-dipropyl-4-allylphenyimino)acenaphtheno-N,N']heptyl octyl nickel (II); [1-(2,6-diphenyl-4-allylphenyimino)-2-(2,6-dimethyl-4-allylphenyimino)-6-phenylacenaphtheno-N,N']hexyl iodo nickel (II); [1-(2,6-dioctyl-4-allylphenyimino)-2-(2,6-dipropyl-4-allylphenyimino)-4-phenyl-5-octylacenaphtheno-N,N']hydrido methyl nickel (II); [1-(2,6-dipropyl-4-allylphenyimino)-2-(2,6-dihexyl-4-allylphenyimino)-5-phenylacenaphtheno-N,N']chloro ethoxy nickel (II); [1-(2,6-diethyl-4-allylphenyimino)-2-(2,6-dimethyl-4 -allylphenyimino)-4-ethylacenaphtheno-N,N']ethyl methoxy copper (II); [1-(2,6-dimethyl-4-allylphenyimino)-2-(2,6-diethyl-4-allylphenyimino)-7-ethylacenaphtheno-N,N']bromo octyl copper (II); [1-(2,6-dipropyl-4-allylphenyimino)-2-(2,6-dihexyl-4-allylphenyimino)acenaphtheno-N,N']ethyl octyl cobalt (II); [1-(2,6-diphenyl-4-allylphenyimino)-2-(2,6-dihexyl-4-allylphenyimino)acenaphtheno-N,N ']pentyl octyl cobalt (II); [1-(2,6-dipropyl-4-allylphenyimino)-2-(2,6-dimethyl-4-allylphenyimino)-3-phenylacenaphtheno-N,N']methyl bromo cobalt (II); [1-(2,6-dihexyl-4-allylphenyimino)-2-(2,6-diethyl-4-allylphenyimino)acenaphtheno-N,N']hexyl ethoxy palladium (II); [1-(2,6 -diphenyl-4-allylphenyimino)-2-(2,6-dipropyl-4-allylphenyimino)-4-propylacenaphtheno-N,N']methoxy butyl palladium (II); [1-(2,6-dipropyl-4-allylphenyimino)-2-(2,6-dihexyl-4-allylphenyimino)acenaphtheno-N,N']propyl iodo palladium (II); [1-(2,6-diethyl-4-allylphenyimino)-2-(2,6-dipropyl-4-allylphenyimino)-8-phenylacenaphtheno-N,N']dihexyl palladium (II); [1-(2,6-dimethyl-4-allylphenyimino)-2-(2,6-dipropyl-4-allylphenyimino)-6-octylacenaphtheno-N,N'] propyl chloro palladium (II); [1-(2,6-dipropyl-4-allylphenyimino)-2-(2,6-dihexyl-4-allylphenyimino) acenaphtheno-N,N']methyl hexyl palladium (II); [1-(2,6-dioctyl-4-allylphenyimino)-2-(2,6-dihexyl-4 -allylphenyimino)acenaphtheno-N,N']ethyl chloro nickel (II).

The catalyst compounds described above may be prepared according to Scheme I:

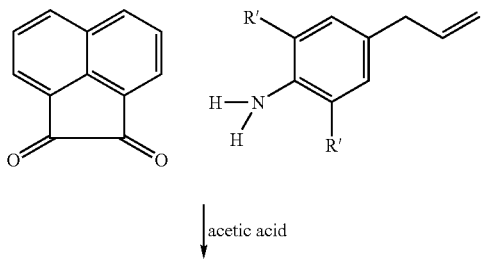

acetic acid

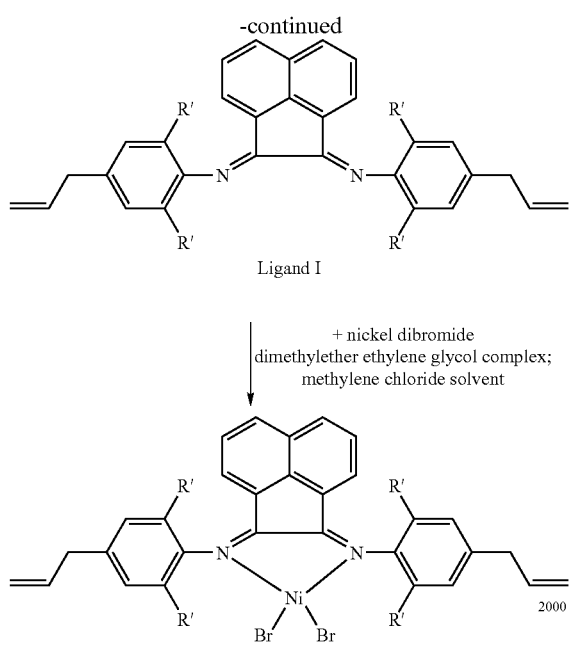

Ligand I

+ nickel dibromide dimethylether ethylene glycol complex; methylene chloride solvent

2000

The first step in preparing invention catalyst precursors is to prepare the ancillary ligand. The ancillary ligand is a substituted acenaphthene. In Scheme I the acenaphthalene is substituted with an imino group; the imino group is substituted with a substituted phenyl group. When R' is isopropyl, the ancillary ligand shown in Scheme I (Ligand I) is called 1,2-bis(4-allyl-2,6-diisopropylphenylimino)acenaphthene. Once this ligand contacts the nickel bromide dimethyl ether ethylene glycol reagent, the free-radical-polymerizable transition metal complex is formed. In some cases, the olefinic unsaturation on the phenyl rings distal to the nickel atom provide the polymerizable functionality to the molecule. The transition metal complex is called [1,2-bis(4-allyl-2,6-diisopropylphenylimino)acenaphthen-N,N']dibromo nickel(II).

Synthesis of the ligand can occur through coupling its two main portions, the aniline and the quinone, such that an imino connection occurs. One way of accomplishing this is shown in Scheme I. The coupling reaction is the acid-catalyzed addition of an aniline to the acenaphthenequinone carbonyl groups (with the loss of water).

Once the two main ligand portions are connected, synthesis of the ancillary ligand is complete. After this, the ligand is simply complexed with an appropriate transition metal halide by mixing the halide and the ligand together. Those of ordinary skill in the art will recognize that other synthetic pathways exist for making these ligands, the resulting transition metal complexes (catalyst precursors), and the polymerized acenaphthene catalyst complexes described below.

Process to Prepare the Polymerized Acenaphthene Catalyst Compounds

The catalyst precursor compound described above is then contacted with a free radical initiator and one or more monomers that can be polymerized by a free radical initiator. This yields a copolymer containing the acenaphtheno-based olefin polymerization catalyst precursor.

A typical transition metal catalyst can be polymerized using the following procedure. 50 ml of a toluene solution with the terminal-unsaturation-containing catalyst, styrene, and AIBN are maintained at 80° C. for 7 hrs. The resulting solution is evaporated and the residue is washed with a mixture of hexane and toluene (2:1) and dried. The solid polymer product is collected. Analogous methods yield the other disclosed polymerized catalysts.

The polymerization typically takes place in solution at a temperature of 30–100° C., 50–90° C., 70–85° C., or 75–85° C. Suitable solvents include toluene, benzene, xylene, and hexane. Desired solvents are selected from those that can dissolve the terminal-unsaturation-containing catalyst.

The polymerization may be performed at atmospheric, sub-atmospheric or super-atmospheric pressures.

Generally, the structure of a catalyst will look like this before copolymerization.

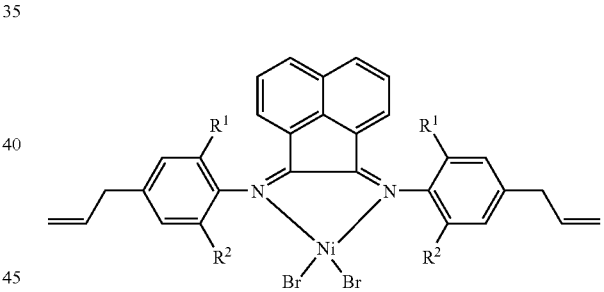

Scheme II illustrates the catalyst polymerization.

Scheme II

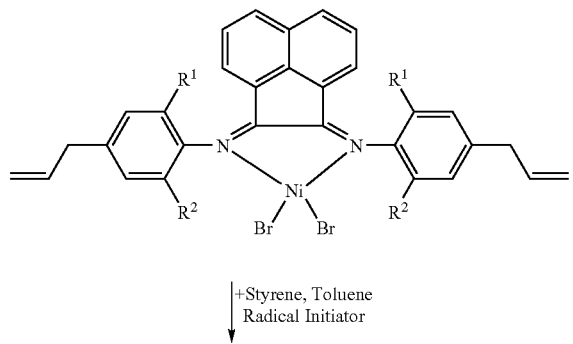

+Styrene, Toluene
Radical Initiator

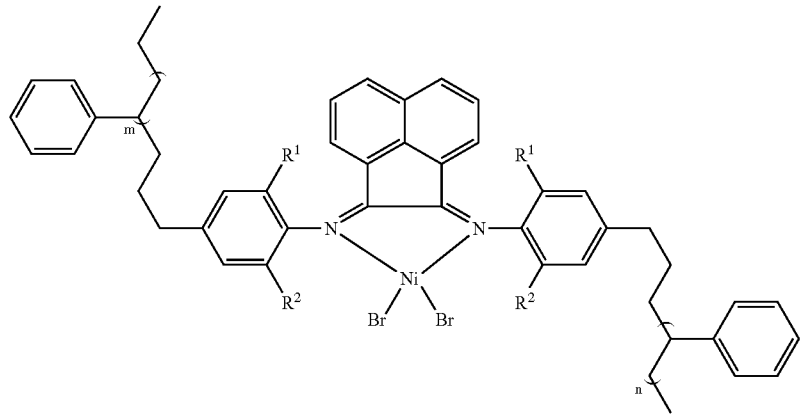

The polymerized catalyst compounds typically have Mw of up to 300,000; 500–150,000; 1,000–100,000; 5,000–75,000; or 10,000–50,000.

Free Radical Initiators

Free radical initiators that are useful in this invention include: (1) thermally decomposable compounds that generate radicals such as azo compounds or organic peroxides; (2) compounds that generate free radicals by non-thermal methods such as photochemical or redox processes; (3) compounds that have inherent radical character such as molecular oxygen; or (4) electromagnetic radiation such as X-rays, electron beams, visible light and ultraviolet-light. Suitable organic peroxide compounds include hydroperoxides, dialkyl peroxides, diacyl peroxides, peroxyesters, peroxydicarbonates, peroxyketals, ketone peroxides and organosulfonyl peroxides. Especially preferred peroxides are t-butyl perbenzoate, dicumyl peroxide, 2,5-dimethyl-2,5-di-tert-butylperoxy-3-hexyne (Lupersol 130), alpha,alpha.-bis(tert-butylperoxy)diisopropyl benzene (VulCup R).

Any free radical initiator or mixture having a 10-hour half-life temperature over 80° C. or their mixtures may function as the initiator in invention processes to prepare supported polymerized catalyst compounds. Generally, the higher the decomposition temperature of the peroxygen compound the better. See pages 66–67 of Modern Plastics, November 1971 for a more complete list of these compounds.

In one embodiment, the free radical initiator is an organic peroxide compound having a half-life, at the reaction temperature, of less than one tenth of the reaction/residence time employed. The free radical initiator is used at concentrations of 1–5% weight percent based on styrene (or other monomer).

The following classes and examples of free-radical initiators are useful in polymerizing invention terminal-unsaturation-containing catalyst precursor compounds:

| | | |
|---|---|---|
| Azo initiators | Dialkyldiazenes | 2,2'-azobis(2-methylpropanenitrile) (AIBN) |
| | | 1,1-azobis(1-cyclohexanenitrile) |
| | | 4,4'-azobis(4-cyanovaleric acid) |
| | | Triphenylmethylazobenzene |
| | Hyponitrites | di-t-butyl hyponitrite |
| | | Dicumyl hyponitrite |
| Peroxides | diacyl peroxides | Dibenzoyl peroxide |
| | | Didodecanoyl peroxide |
| | | Diacetyl peroxide |
| | dialkyl peroxydicarbonates | Diisopropyl ester |
| | | Dicyclohexyl ester |
| Peresters | | |
| | alkyl hydroperoxides | Cumyl hydroperoxide |
| | | t-butyl hydroperoxide |
| | dialkyl peroxides | Dicumyl peroxide |
| | | di-t-butyl peroxide |
| | inorganic peroxides | Hydrogen peroxide |
| | | persulfate |

Monomers Polymerizable by a Free Radical Initiator

Monomers that can be polymerized by a free radical process include ethylene, 1,3-butadiene, isoprene, styrene, alkyl styrene, isobutylene, vinyl chloride, vinylidene chloride, vinyl fluoride, tetrafluoroethylene, vinyl esters, acrylic esters, methacrylic esters, acrylonitrile, and propylene. Therefore, any of these can be copolymerized with the catalyst compound containing the terminal unsaturation. For example, selecting isoprene for copolymerization results in a catalyst/isoprene copolymer.

Process to Polymerize Olefins Using the Polymerized Catalyst Compound

Combining the polymerized catalyst compounds described above with one or more activators forms an olefin-polymerization catalyst system.

For purposes of this disclosure, the terms activator and cocatalyst are used interchangeably. An activator functions to remove an abstractable ligand X from the transition metal. After activation the transition metal is left with an empty coordination site at which incoming α-olefin can coordinate before it is incorporated into the oligomer or polymer. Any reagent that can so function without destroying the commercial viability of the oligomerization or polymerization process is suitable for use as an activator or cocatalyst in this invention.

Invention-suitable activators include Lewis acid, non-coordinating ionic activators or ionizing activators, or any other compound including Lewis bases, aluminum alkyls, conventional-type cocatalysts, and their combinations that can convert a catalyst compound into a catalytically active cation. This invention can use alumoxane or modified alumoxane as an activator, and can also use ionizing activators, neutral or ionic, such as tri (n-butyl) ammonium tetrakis (pentafluorophenyl) boron, a trisperfluorophenyl boron metalloid precursor or a trisperfluoronaphthyl boron metalloid precursor, polyhalogenated heteroborane anions (WO 98/43983), or their combinations. This invention can use these compounds as activators if they can ionize the catalyst metal compound or if the catalyst metal compound can be pre-reacted to form a compound that these activators can ionize.

One class of invention-suitable activators includes alumoxanes such as methylalumoxane, modified methylalumoxane, ethylalumoxane, etc.; aluminum alkyls such as trimethyl aluminum, triethyl aluminum, triisopropyl aluminum, etc.; alkyl aluminum halides such as diethyl aluminum chloride, etc.; and alkylaluminum alkoxides.

An alumoxane component useful as an activator is typically an oligomeric aluminum compound represented by the general formula (R"—Al—O)$_n$, which is a cyclic compound, or R"(R"—Al—O)$_n$AlR"$_2$, which is a linear compound. Generally, R" is independently a C$_1$–C$_{20}$ alkyl radical, for example, methyl, ethyl, propyl, butyl, pentyl, isomers thereof, etc., and "n" is an integer from 1–50. Those of ordinary skill in the art recognize that alumoxanes in which R" is methyl and "n" is at least four are particularly useful: methylalumoxane and modified methylalumoxanes. For further descriptions see, EP 279586, EP 561476, WO94/10180, and U.S. Pat. Nos. 4,665,208, 4,908,463, 4,924,018, 4,952,540, 4,968,827, 5,041,584, 5,103,031, 5,157,137, 5,235,081, 5,248,801, 5,329,032, 5,391,793, and 5,416,229.

Those of ordinary skill in the art know how to prepare alumoxanes and modified alumoxanes. See U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publication WO 94/10180.

Another class of invention-suitable activators includes aluminum alkyl components represented by the general formula R"AlZ$_2$ where R" is defined above for alumoxanes, and each Z is independently R" or a different univalent anionic ligand such as halogen (Cl, Br, I), alkoxide (OR"), etc. Particularly useful aluminum alkyls include triethylaluminum, diethylaluminum chloride, triisobutylaluminum, tri-n-octylaluminum, etc.

When alumoxane or aluminum alkyl activators are used, the catalyst-precursor-to-activator molar ratio is from about 1:1000 to 10:1; alternatively, 1:500 to 1:1; or 1:300 to 1:10.

Yet another class of invention-suitable activators includes discrete ionic activators. These are especially useful when both abstractable ligands are hydride or hydrocarbyl. [Me$_2$PhNH][B(C$_6$F$_5$)$_4$], [Bu$_3$NH][BF$_4$], [NH$_4$][PF$_6$], [NH$_4$][SbF$_6$], [NH$_4$][AsF$_6$], [NH$_4$][B(C$_6$H$_5$)$_4$] or Lewis acidic activators such as B(C$_6$F$_5$)$_3$ or B(C$_6$H$_5$)$_3$ are examples of discrete ionic activators. Discrete ionic activators provide for an activated catalyst site and a relatively non-coordinating (or weakly coordinating) anion. Activators of this type are well known, see for instance W. Beck, et al., Chem. Rev., vol. 88, p. 1405–1421 (1988); S. H. Strauss, Chem. Rev., vol. 93, p. 927–942 (1993); U.S. Pat. Nos. 5,198,401; 5,278,119; 5,387,568; 5,763,549; 5,807,939; 6,262,202; and WO93/14132; WO99/45042; WO01/30785; and WO01/42249. These activator types also function when X is not hydrocarbyl, if they are used with a compound capable of alkylating the metal such as an alumoxane or aluminum alkyl.

When a discrete ionic activator is used, the catalyst-precursor-to-activator molar ratio is from 10:1 to 1:10; 5:1 to 1:5; 2:1 to 1:2; or 1.2:1 to 1:1.

Another class of invention-suitable activators includes those described in PCT publication WO 98/07515 such as tris(2,2',2"-nonafluorobiphenyl) fluoroaluminate. Combining activators from different classes suits this invention, for example, alumoxanes and ionizing activators in combinations, see for example, EP-B1 0 573 120, PCT publications WO 94/07928 and WO 95/14044 and U.S. Pat. Nos. 5,153,157 and 5,453,410. WO 98/09996 describes activating catalyst compounds with perchlorates, periodates, and iodates including their hydrates. WO 98/30602 and WO 98/30603 describe the use of lithium (2,2'-bisphenyl-ditrimethylsilicate). 4THF as an activator for a catalyst compound. WO 99/18135 describes the use of organo-boron-aluminum activators. EP-B1-0 781 299 describes using a silylium salt in combination with a non-coordinating compatible anion. Also, activation methods using irradiation (see EP-B1-0 615 981), electrochemical oxidation, etc., are also useful for activating catalyst precursors. Other activators or activating methods are described in, for example, U.S. Pat. Nos. 5,849,852, 5,859,653 and 5,869,723 and WO 98/32775, WO 99/42467 (dioctadecylmethylammonium-bis(tris(pentafluorophenyl)borane) benzimidazolide).

Combining modified alumoxanes with invention polymerized catalyst compounds forms a catalyst system. MMAO3A (modified methyl alumoxane in heptane, commercially available from Akzo Chemicals, Inc., Holland, under the trade name Modified Methylalumoxane type 3A) is such an example. Combining the alumoxanes disclosed in U.S. Pat. No. 5,041,584 with invention polymerized catalyst compounds forms a catalyst system, as well.

Polymerization Processes (TM Catalyzed)

Some of the catalyst systems described above are suitable for use in solution polymerization processes, some for use in gas-phase processes, and some in slurry processes. Some of the catalyst systems above are suitable for use in combinations of those processes.

In invention polymerization or oligomerization processes using invention catalyst systems, the process temperature can be −100° C. to 300° C., −20° C. to 200° C., or 0° C. to 150° C. Given one of these temperature ranges, the following ethylene oligomerization pressures (gauge) are useful: 0 kPa–35 MPa or 500 kPa–15 MPa.

In polymerization or oligomerization processes using invention catalyst systems and any of the process conditions described above, whether the selected process is solution, slurry, gas-phase or an amalgamation of these, the process can employ one or more, C$_2$–C$_{30}$ monomers. Alternatively, C$_2$–C$_{12}$ or C$_2$–C$_8$ monomers are suitable. Specific examples of invention-suitable monomers include one or more of ethylene, propylene, butene-1, pentene-1, 4-methyl-pentene-1, hexene-1, octene-1, decene-1, 3-methyl-pentene-1, and cyclic olefins, or their combinations. Other monomers can include vinyl monomers, diolefins such as dienes, polyenes, norbornene, norbornadiene, vinyl norbornene, ethylidene norbornene monomers. Alternatively, invention polymerization processes produce homopolymers or copolymers of ethylene or propylene.

In polymerization or oligomerization processes using invention catalyst systems and any of the process conditions described above, polymerization with ethylene and at least two different comonomers forms terpolymers. Invention comonomers comprise a combination of any of the monomers described above or of $C_2$–$C_{30}$ or $C_4$–$C_8$, α-olefin monomers, optionally with at least one diene monomer. Terpolymers include combinations such as propylene/but-1-ene/hex-1-ene, propylene/but-1-ene/ethylene, propylene/ethylene/hex-1-ene, propylene/butene/norbornene, propylene/butene/decadiene, and the like. For purposes of this disclosure, nomenclature such as "but-1-ene", which indicates that the olefinic unsaturation in the butene molecule begins at the first atom in the butene carbon chain, is equivalent to "butene-1".

Invention oligomerization or polymerization processes can be run in the presence of various liquids, particularly aprotic organic liquids. In some embodiments the catalyst system is insoluble in most solvents; and thus, the polymerization will be slurry phase rather than solution phase. Liquid-suitable invention catalyst systems include alkanes, alkenes, cycloalkanes, selected halogenated hydrocarbons, aromatic hydrocarbons, and in some cases, hydrofluorocarbons. Useful solvents specifically include hexane, toluene, cyclohexane, and benzene.

Gas-Phase Polymerization

In polymerization or oligomerization processes using invention catalyst systems, the reactor pressure in a gas-phase process can vary from 69 kPa–3.5 MPa, alternatively from 690 kPa–3.5 MPa, from 1379 kPa–2.8 MPa, or from 1.7–2.414 MPa. Invention processes and catalyst systems can use suitable gas-phase polymerization processes; some of these processes are described below.

In gas-phase, polymerization or oligomerization processes using invention catalyst systems, given a particular reactor pressure range, the reactor temperature can vary from 30–120° C., alternatively from 60–115° C., from 70–110° C., or from 70–95° C. The reactor temperature is typically between 70–105° C. for high-density polyethylene.

In gas-phase systems, polymerization or oligomerization processes using invention catalyst systems, monomer partial pressure influences catalyst system productivity. Primary monomer concentration, such as ethylene or propylene, is from 25–90 mole percent, and its partial pressure is from 138–517kPa or 517 kPa–2.1 MPa. These conditions suit invention gas-phase, polymerization or oligomerization processes. Also, in some systems, comonomer presence yields productivity increases.

Gas-phase, polymerization or oligomerization processes using invention catalyst systems can produce 227–90,900 kg/hr of polymer, alternatively, 227–455 kg/hr, 227–4540 kg/hr, 227–11,300 kg/hr, 227–15,900 kg/hr, 227–22,700 kg/hr, and alternatively 29,000 kg/hr–45,500 kg/hr, or 45,500 kg/hr or more.

Gas-phase, polymerization or oligomerization processes using invention catalyst systems can use the processes described in U.S. Pat. Nos. 5,627,242, 5,665,818 and 5,677, 375, and European publications EP-A-0 794 200, EP-A-0 802 202 and EP-B-634 421.

In some gas-phase, polymerization or oligomerization processes using invention catalyst systems, the reactor receives the liquid or solution catalyst system in its liquid form at a resin-particle-lean zone. For information on how to introduce a liquid catalyst system into a fluidized bed polymerization reactor at a resin-particle-lean zone, see U.S. Pat. No. 5,693,727.

Gas-phase, polymerization or oligomerization processes using invention catalyst systems can operate with scavengers. Typical scavengers include trimethyl aluminum, triisobutyl aluminum, an excess of alumoxane or modified alumoxane, triethylaluminum, tri-n-hexylaluminum, diethyl aluminum chloride, dibutyl zinc and the like. PCT publication WO 96/08520 and U.S. Pat. No. 5,712,352 describe processes using these scavengers. Invention, gas-phase processes or catalyst systems can use these processes. Alternatively, gas-phase, polymerization, or oligomerization processes using invention catalyst systems can operate in the absence of or essentially free of scavengers.

Slurry Polymerization

In polymerization or oligomerization processes using invention catalyst systems, slurry polymerization processes generally use pressures of 103–5068 kPa and temperatures of 0–120° C. Invention processes and catalyst systems can use suitable slurry polymerization processes; some of these processes are described below.

Typically, in a slurry polymerization, a suspension of solid, particulate polymer forms in a liquid polymerization medium to which ethylene (or α-olefinic monomer) and comonomers, along with catalyst, has been added. This suspension intermittently or continuously discharges from the reactor, after which the process separates the polymer from the volatile components and recycles them (optionally after a distillation) to the reactor. The liquid employed in the polymerization medium typically comprises a $C_3$–$C_7$ alkane, alternatively a branched alkane. The medium should be liquid and relatively inert under the polymerization conditions. For propane media, process temperatures and pressures are usually above the media's critical temperature and pressure. The processes can use hexane or isobutane media, as well.

One slurry polymerization process is a particle-form polymerization. It is a process where the temperature remains below the temperature at which the polymer appreciably dissolves in the reaction medium. Such techniques are well known in the art. U.S. Pat. No. 3,248,179. Particle-form process temperatures range from 85° C.–110° C. Two other slurry polymerization varieties employ a loop reactor or a plurality of stirred reactors in series, parallel, or combinations thereof. These reactors can have cooling or not and can employ refrigerated or unrefrigerated monomer feeds. Non-limiting examples of slurry processes include continuous-loop and stirred-tank processes. Also, U.S. Pat. No. 4,613, 484 describes other examples of slurry processes.

Slurry processes can use a continuous-loop reactor. The process regularly injects the catalyst, as a slurry in a compatible solvent or as a dry, free-flowing powder, into the reactor loop. The loop contains a circulating slurry of growing polymer particles in a diluent of isobutane containing monomer and comonomer. If desired, this process can control molecular weight with hydrogen. The reactor is maintained at a pressure of 3.620–4.309 MPa and at a temperature of 60–104° C. depending on the desired polymer density. Reaction heat is removed from the reactor through the loop wall since much of the reactor vessel is a double-jacketed pipe. The slurry discharges from the reactor at regular intervals or continuously. It discharges into a heated, low-pressure flash vessel, rotary dryer, and nitrogen purge column, in sequence, to remove isobutane diluent and all unreacted monomer and comonomer. The resulting hydrocarbon-free powder is then compounded for use in various applications.

Polymerization or oligomerization processes using invention catalyst systems and using slurry polymerization conditions can produce 1–100,000 kg polymer/hr, 907–100,000 kg/hr, 2268–100,000 kg/hr, 4540–100,000 kg/hr, 6804–100,000 kg/hr, 11,340–100,000 kg/hr, or 45,500–100,000 kg/hr.

Polymerization or oligomerization processes using invention catalyst systems and using slurry polymerization conditions can use total reactor pressures in the range of 2758–5516 kPa, 3103–4827 kPa, 3448–4482 kPa, or 3620–4309 kPa.

Polymerization or oligomerization processes using invention catalyst systems and using slurry polymerization conditions can use concentrations of predominant monomer in the reactor liquid medium of 1–10 wt %, 2–7 wt %, 2.5–6 wt %, or 3–6 wt %.

As with gas-phase polymerization conditions, polymerization or oligomerization processes using invention catalyst systems and slurry polymerization conditions can use slurry process variants that include or exclude scavengers.

Applications of Invention Polyolefins

Invention processes prepare homo- and co-polymer polyethylene useful for formulating adhesives and other materials.

Formulations

In some embodiments, the polymer produced by this invention may be blended with one or more other polymers such as thermoplastic polymer(s) and elastomer(s).

A thermoplastic polymer is a polymer that can be melted by heating and then cooled without appreciable change in properties. Thermoplastic polymers typically include polyolefins, polyamides, polyesters, polycarbonates, polysulfones, polyacetals, polylactones, acrylonitrile-butadiene-styrene resins, polyphenylene oxide, polyphenylene sulfide, styrene-acrylonitrile resins, styrene maleic anhydride, polyimides, aromatic polyketones, or mixtures of two or more of the above. Specific polyolefins include polymers comprising one or more, linear, branched, or cyclic, $C_2$–$C_{40}$ olefins, preferably polymers comprising ethylene or propylene copolymerized with one or more, $C_3$–$C_{40}$ olefins, $C_3$–$C_{20}$ α-olefins, or $C_3$–$C_{10}$ α-olefins.

Elastomers include all natural and synthetic rubbers, including those defined in ASTM D1566. Examples of elastomers include ethylene propylene rubber, ethylene propylene diene monomer rubber, styrenic block copolymer rubbers (including SI, SIS, SB, SBS, SIBS and the like, where S=styrene, I=isobutylene, and B=butadiene), butyl rubber, halobutyl rubber, copolymers of isobutylene and para-alkylstyrene, halogenated copolymers of isobutylene and para-alkylstyrene, natural rubber, polyisoprene, copolymers of butadiene with acrylonitrile, polychloroprene, alkyl acrylate rubber, chlorinated isoprene rubber, acrylonitrile chlorinated isoprene rubber, polybutadiene rubber (both cis and trans).

In another embodiment polymer produced by this invention is combined with one or more isotactic polypropylenes; highly isotactic polypropylenes; syndiotactic polypropylenes; random copolymers of propylene and ethylene or butene or hexene; polybutenes; ethylene vinyl acetate; low-density polyethylenes (density 0.915 to 0.935 g/cm$^3$); linear-low-density polyethylenes; ultra-low-density polyethylenes (density 0.86 to 0.90 g/cm$^3$); very-low-density polyethylenes (density 0.90 to 0.915 g/cm$^3$); medium-density polyethylenes (density 0.935 to 0.945 g/cm$^3$); high-density polyethylenes (density 0.945 to 0.98 g/cm$^3$); ethylene vinyl acetates; ethylene methyl acrylates; copolymers of acrylic acid, polymethylmethacrylate, or any other polymers polymerizable by high-pressure free radical processes; polyvinylchlorides, polybut-1-enes; isotactic polybutenes; ABS resins; ethylene-propylene rubbers (EPR); vulcanized EPRs; EPDMs; block copolymers; styrenic block copolymers; polyamides; polycarbonates; PET resins; crosslinked polyethylenes; copolymers of ethylene and vinyl alcohol (EVOH); or polymers of aromatic monomers such as polystyrene; poly-1-esters; polyacetal; polyvinylidine fluoride; polyethylene glycols; or polyisobutylenes.

In another embodiment, elastomers are blended with the polymer produced by this invention to form rubber-toughened compositions. In some embodiments, the rubber toughened composition is a two (or more) phase system where the elastomer is a discontinuous phase and the polymer produced by this invention is a continuous phase. This blend may be combined with tackifiers or other additives as is known in the art.

In another embodiment, the polymer produced by this invention may be blended to form impact copolymers. In some embodiments, the blend is a two (or more) phase system with a discontinuous phase and a continuous phase. This blend may be combined with tackifiers or other additives as is known in the art.

In some embodiments invention polymers are combined with metallocene polyethylenes (mPEs) or metallocene polypropylenes (mPPs). The mPE and mPP homopolymers or copolymers are typically produced using mono- or bis-cyclopentadienyl transition metal catalysts in combination with alumoxane or a non-coordinating anion activator in solution, slurry, high-pressure, or gas-phase conditions. The supported or unsupported catalyst and activator may have substituted or unsubstituted cyclopentadienyl rings. Exxon-Mobil Chemical Company (Baytown, Tex.) produces several commercial products with such catalyst and activator combinations. These are commercially available under the tradenames EXCEED™, ACHIEVE™, and EXACT™. For more information on the methods and catalyst-activator pairs used to produce such homopolymers and copolymers, see WO 94/26816; WO 94/03506; EPA 277,003; EPA 277, 004; U.S. Pat. No. 5,153,157; U.S. Pat. No. 5,198,401; U.S. Pat. No. 5,240,894; U.S. Pat. No. 5,017,714; CA 1,268,753; U.S. Pat. No. 5,324,800; EPA 129,368; U.S. Pat. No. 5,264, 405; EPA 520,732; WO 92 00333; U.S. Pat. No. 5,096,867; U.S. Pat. No. 5,507,475; EPA 426 637; EPA 573 403; EPA 520 732; EPA 495 375; EPA 500 944; EPA 570 982; WO91/09882; WO94/03506 and U.S. Pat. No. 5,055,438.

In some embodiments invention polymers are present in the above blends, at from 10–99 wt %, 20–95 wt %, 30–90 wt %, 40–90 wt %, 50–90 wt %, 60–90 wt %, 70–90 wt %. (Based upon the weight of the polymers in the blend.)

The blends described above may be produced by mixing the invention polymers with one or more polymers (as described above), by connecting reactors together in series to make reactor blends, or by using more than one catalyst in the same reactor to produce multiple species of polymer. The polymers can be mixed together before being put into the extruder or may be mixed in the extruder.

Any of the above polymers may be functionalized, which means that the polymer has been reacted with an unsaturated acid or anhydride. Unsaturated acids and anhydrides include any unsaturated organic compound containing at least one double bond and at least one carbonyl group. Representative acids include carboxylic acids, anhydrides, esters and their metallic and non-metallic salts. In some embodiments the organic compound contains an ethylenic unsaturation conjugated with a carbonyl group (—C═O). Examples include maleic, fumaric, acrylic, methacrylic, itaconic, crotonic, alpha.methyl crotonic, and cinematic acids as well as their anhydrides, esters and salt derivatives. The unsaturated acid or anhydride is present at 0.1–10 wt %, 0.5–7 wt % or 1–4 wt %, based upon the weight of the hydrocarbon resin and the unsaturated acid or anhydride.

Tackifiers may be blended with invention polymers or with blends of invention polymers (as described above). Examples of useful tackifiers include aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, and hydrogenated rosin esters. In some embodiments, the tackifier is hydrogenated. In other embodiments, the tackifier is non-polar. (Non-polar means that the tackifier is substantially free of monomers having polar groups. Some tackifier compositions limit the polar-group content to 5 wt % or less, alternatively, 2 or 0.5 wt % or less.) In some embodiments the tackifier has a softening point (Ring and Ball, as measured by ASTM E-28) of 80–40 or 100–30° C. In some embodiments, the tackifier is functionalized, which means that the hydrocarbon resin has been contacted with an unsaturated acid or anhydride. Some embodiments select unsaturated acids or anhydrides from any unsaturated organic compound containing at least one double bond and at least one carbonyl group. Representative acids include carboxylic acids, anhydrides, esters and their salts, both metallic and non-metallic. In some embodiments the organic compound contains an ethylenic unsaturation conjugated with a carbonyl group (—C═O). Examples include maleic, fumaric, acrylic, methacrylic, itaconic, crotonic, alpha.m-ethyl crotonic, and cinnamic acids as well as their anhydrides, esters and salt derivatives. The unsaturated acid or anhydride is present at 0.1 wt %, alternatively 0.5 wt % or 1 wt %, based upon the weight of the hydrocarbon resin and the unsaturated acid or anhydride.

Invention polymers, or their blends, may further comprise a crosslinking agent. Particularly suitable crosslinking agents include those having functional groups that can react with the acid or anhydride group. Alcohols, multiols, amines, diamines, and triamines belong to a nonexclusive list of crosslinking agents. Examples of useful crosslinking agents include polyamines such as ethylenediamine, diethylenetriamine, hexamethylenediamine, diethylaminopropylamine, and menthanediamine.

Invention polymers, or their blends, may further comprise typical additives known in the art such as fillers, cavitating agents, antioxidants, surfactants, adjuvants, plasticizers, antiblock additives, color masterbatches, pigments, dyes, processing aids, UV stabilizers, neutralizers, lubricants, waxes, or nucleating agents. Typically, these additives are present in amounts well known to be effective in the art: such as 0.001–10 wt %.

Specific fillers, cavitating agents, or nucleating agents include titanium dioxide, calcium carbonate, barium sulfate, silica, silicon dioxide, carbon black, sand, glass beads, mineral aggregates, talc, clay, etc.

Effective antioxidants include phenolic antioxidants, such as Irganox 1010, Irganox, 1076 both available from Ciba-Geigy. Effective oils include paraffinic or naphthenic oils, such as Primol 352 or Primol 876 available from Exxon-Mobil Chemical France, S. A. (Paris, France) and aliphatic naphthenic oils, white oils, etc.

Effective plasticizers and adjuvants include mineral oils, polybutenes, phthalates, etc. Plasticizers include phthalates such as diisoundecyl phthalate (DIUP), diisononylphthalate (DINP), dioctylphthalates (DOP), and polybutenes.

Effective processing aids, lubricants, waxes, and oils include low molecular weight products such as wax, oil or low Mn polymer, (low meaning Mn below 5000, below 4000, below 3000, or below 2500). Effective waxes include polar or non-polar waxes, functionalized waxes, polypropylene waxes, polyethylene waxes, and wax modifiers. Effective functionalized waxes include those modified with an alcohol, an acid, or a ketone.

Some invention polymers are functionalized after polymerization. Functionalized means that the polymer has been contacted with an unsaturated acid or anhydride. Suitable unsaturated acids or anhydrides include any unsaturated organic compound comprising one double bond and one carbonyl group. Representative acids include carboxylic acids, anhydrides, esters and their salts, both metallic and non-metallic. Some useful organic compound contains an ethylenic unsaturation conjugated with a carbonyl group (—C═O). Examples include maleic, fumaric, acrylic, methacrylic, itaconic, crotonic, alpha.methyl crotonic, and cinnamic acids as well as their anhydrides, esters and salt derivatives. The unsaturated acid or anhydride is present at 0.1–10 wt %, alternatively 0.5–7 wt % or 1–4 wt % based upon the weight of the hydrocarbon resin and the unsaturated acid or anhydride. Specific examples include waxes modified by methyl ketone, maleic anhydride, or maleic acid. Suitable low Mn polymers include lower α-olefins polymers such as propylene, butene, pentene, hexene, etc. Some embodiments select the polymer such that it includes polybutene having an Mn of less than 1000.

APPLICATIONS

Invention polymers (and their blends as described above) whether formed in situ or by physical blending are used in any known thermoplastic or elastomer application. Examples include uses in molded parts, films, tapes, sheets, tubing, hose, sheeting, wire and cable coating, adhesives, shoe soles, bumpers, gaskets, bellows, films, fibers, elastic fibers, nonwoven materials, spunbond materials, sealants, surgical gowns, and medical devices.

Adhesives

Invention polymers or their blends can be used as adhesives, either alone or combined with tackifiers. Preferred tackifiers are described above. The tackifier is typically present at about 1 wt % to about 50 wt %, based upon the weight of the blend, more preferably 10 wt % to 40 wt %, even more preferably 20 wt % to 40 wt %. Other additives, as described above, may be added also.

Invention-polymer-based adhesives can be used in any adhesive application, such as disposable items, packaging, laminates, pressure-sensitive adhesives, tapes labels, wood binding, paper binding, non-woven materials, road marking materials, reflective coatings, etc. In some embodiments Invention-polymer-based adhesives can be used for chassis construction in disposable diapers and napkins, elastic attachment in disposable-goods, and converting, packaging, labeling, bookbinding, woodworking, and other assembly applications. Specific articles include diaper liquid-transfer layers, diaper leg elastics, diaper frontal tapes, diaper standing-leg cuffs, feminine-napkin adhesive strips and perishable product packaging. Specific applications include laminations for diaper outer covers, diaper elastic cuffs, filter materials, filter masks, surgical gowns, and surgical drapes; core stabilization for diapers and feminine-napkins; diaper chassis construction; and filtration system bonding.

The invention-polymer-based adhesives described above may be applied to any substrate. Useful substrates include wood, paper, cardboard, plastic, thermoplastic, rubber, metal, metal foil (such as aluminum foil and tin foil), metallized surfaces, cloth, non-woven cloth (particularly polypropylene cloths), spunbonded fiber, cardboard, stone, plaster, glass (including silicon oxide ($SiO_x$) coatings applied by evaporating silicon oxide onto a film surface), foam, rock, ceramic, film, polymer foam (such as polyurethane foam), coated substrate (such as those coated with inks, dyes, pigments), polyvinylidene chloride, etc. or their combinations. Additional useful substrates include polyethylene, polypropylene, polyacrylates, acrylics, polyethylene terephthalate, or any of the polymers listed above as suitable for blends. Any of the above substrates may be modified by corona treatment, electron beam irradiation, gamma irradiation, microwave, or silanization.

Films

Invention polymers and their blends can form mono- or multi-layer films. These films may be formed by any of the conventional techniques known in the art including extrusion, co-extrusion, extrusion coating, and lamination, blowing and casting. These films may be formed by the flat film or tubular process; afterwards they may be oriented in a uniaxial or in two mutually perpendicular directions in the film's plane. One or more of the layers of the film may be oriented in the transverse or longitudinal directions to the same or different extents. This orientation may occur before or after bringing the individual layers together. For example, a polyethylene layer can be extrusion coated or laminated onto an oriented polypropylene layer, or the polyethylene and polypropylene can be coextruded into a film, then oriented. Likewise, oriented polypropylene could be laminated to oriented polyethylene or oriented polyethylene could be coated onto polypropylene. Further orientation could follow, if desired. Film orientation in the machine direction (MD) is typically at a ratio of 1–15 or 5–7, while orientation in the transverse direction (TD) is typically at a ratio of 1–15 or 7–9. But in some embodiments, MD and TD orientation ratios are the same.

In another embodiment, the layer comprising the invention polymer compositions (or their blends) may be combined with one or more other layers. The other layer(s) may be any of those layers typically included in multilayer films. For example, the other layer or layers may be polyolefins (such as homopolymers or copolymers of $C_2$–$C_{40}$ olefins or $C_2$–$C_{20}$ olefins) or copolymers of α-olefins and other olefins (including α-olefins and ethylene). Specific polyolefins for use as other layers include homopolyethylene; homopolypropylene; propylene copolymerized with ethylene or butene; and ethylene copolymerized with one or more of propylene, butene or hexene, and optional dienes. Specific examples include thermoplastic polymers such as ultra-low-density polyethylene, very-low-density polyethylene, linear-low-density polyethylene, low-density polyethylene, medium-density polyethylene, high-density polyethylene, polypropylene, isotactic polypropylene, highly isotactic polypropylene, syndiotactic polypropylene, random copolymer of propylene and ethylene, butene, hexene, elastomers such as ethylene propylene rubber, ethylene propylene diene monomer rubber, neoprene, and blends of thermoplastic polymers and elastomers, such as for example, thermoplastic elastomers and rubber toughened plastics.

Likewise, the other layer or layers may be polar polymers. Specific polar polymers include homopolymers and copolymers of esters, amides, acetates, anhydrides, copolymers of $C_2$–$C_{20}$ olefins (such as ethylene and/or propylene and/or butene with one or more polar monomers such as acetates, anhydrides, esters, alcohol, or acrylics). Specific examples include polyesters, polyamides, ethylene-vinyl-acetate copolymers, and polyvinyl chloride.

Likewise, the other layer or layers may be cationic polymers. Specific cationic polymers include polymers or copolymers of geminally disubstituted olefins, α-heteroatom-olefins, or styrenic monomers. Specific geminally disubstituted olefins include isobutylene, isopentene, isoheptene, isohexane, isooctene, isodecene, and isododecene. Specific α-heteroatom-olefins include vinyl ether and vinyl carbazole. Specific styrenic monomers include styrene, alkyl styrene, para-alkyl styrene, α-methyl styrene, chloro-styrene, and bromo-para-methyl styrene. Specific examples of cationic polymers include butyl rubber, isobutylene copolymerized with para methyl styrene, polystyrene, and poly-α-methyl styrene.

Finally, other specific layers can be paper, wood, cardboard, metal, metal foils (such as aluminum foil and tin foil), metallized surfaces, glass (including silicon oxide ($SiO_x$) coatings applied by evaporating silicon oxide onto a film surface), fabric, spunbonded fibers, and non-wovens (particularly polypropylene spun bonded fibers or non-wovens), and substrates coated with inks, dyes, pigments, polyvinylidene chloride and the like.

The films may vary in thickness depending on the intended application; films from 1–250 μm thick are usually suitable. Packaging films are usually from 10–60 μm thick. Sealing layers are typically 0.2–50 μm. There may be a sealing layer on both the inner and outer surfaces of the film or the sealing layer may be present on only the inner or the outer surface. Additives such as antiblock additives, antioxidants, pigments, fillers, processing aids, UV stabilizers, neutralizers, lubricants, surfactants and/or nucleating agents may also be present in one or more layers in the films. Specific additives include silicon dioxide, titanium dioxide, polydimethylsiloxane, talc, dyes, wax, calcium stearate, carbon black, low-molecular-weight resins, and glass beads. In some embodiments one or more layers may be modified by corona treatment, electron beam irradiation, gamma irradiation, or microwave. In some embodiments one or both of the surface layers is modified by corona treatment.

The films described herein may also comprise from 5–60 wt % of a hydrocarbon resin, based upon the weight of the polymer and the resin. The resin may be combined with the polymer of the seal layer(s) or may be combined with the polymer in the core layer(s). The resin softening point is 100–200° C. or 130–180° C. Preferred hydrocarbon resins include those described above. The films comprising a hydrocarbon resin may be oriented in uniaxial or biaxial directions to the same or different degrees.

The films described above may be used as stretch or cling films. Stretch-cling films are used in various bundling, packaging and palletizing operations. A number of well-known tackifying additives impart cling properties to or improve the cling properties of a particular film. Common tackifying additives include polybutenes, terpene resins, alkali metal stearates, and hydrogenated rosins and rosin esters. Corona discharge can also modify film properties. Some polymers (such as ethylene-methylacrylate copolymers) do not need cling additives and can be used as cling layers without tackifiers. Stretch-clings films may comprise a slip layer comprising any suitable polyolefin or combination of polyolefins such as polyethylene, polypropylene, copolymers of ethylene and propylene, and polymers obtained from ethylene or propylene copolymerized with minor amounts of other olefins, particularly $C_4$–$C_{12}$ olefins. Polypropylene and linear low density polyethylene (LLDPE) work well. Suitable polypropylene is normally solid and isotactic (greater than 90% hot heptane insolubles) and has wide ranging melt flow rates (0.1–300 g/10 min). Additionally, the slip layer may include one or more, anticling (slip or antiblock) additives that may be added during polyolefin production blended in afterwards to improve the layer's slip properties. Such additives are well-known in the art and include, for example, silicas, silicates, diatomaceous earths, talcs, and various lubricants. These additives are typically used in amounts ranging from 100–20,000 ppm or 500–10,000 ppm by weight based upon the weight of the slip layer. The slip layer may, if desired, also include one or more other additives as described above.

Polymer products can be used for nonwovens, sealing layers, oriented polypropylene, and high-clarity thermoforming materials.

Low molecular weight varieties of high-pressure propylene homo- and co-polymers can be used for hot melt and pressure sensitive adhesives.

Invention processes can use finely divided, supported catalysts to prepare propylene/1-hexene copolymers with greater than 1.0 mole % hex-1-ene. In addition to finely divided supports, invention processes can use fumed silica supports in which the support particle size is small enough to form a colloid in the reaction media.

End Use Articles

Laminates comprising invention polymers can be used as a thermoformable sheet where the substrate is either sprayed or injection molded to couple it with the ionomer/tie-layer laminate sheet. The composite if formed into the desired shape to form the article, or composite article. Various types of substrate materials to form highly desirable articles. The laminate can be used with plastic substrates such as homopolymers, copolymers, foams, impact copolymers, random copolymers, and other applications. Specifically, some articles in which the present invention can be incorporated are the following: vehicle parts, especially exterior parts such as bumpers and grills, rocker panels, fenders, doors, hoods, trim, and other parts can be made from the laminates, composites and methods of the invention.

Other articles can also be made, for example, counter tops, laminated surface counter tops, pool liners, pool covers, boat covers, boat sails, cable jacketing, motorcycles, snowmobiles, outdoor vehicles, marine boat hulls, canoe interiors and exteriors, luggage, clothing, fabric (combined with non-wovens), tent materials, GORE-TEX™ (microporous filipolytetrafluoroethylene), Gamma-radiation resistant applications, electronic housings (TV's, VCR's and computers), wood replacement for decks and other outdoor building materials, prefab buildings, synthetic marble panels for construction, wall coverings, hopper cars, floor coating, polymer-wood composites, vinyl tiles, bath, shower, toilet applications and translucent glass replacement, sidings, lawn and outdoor furniture, appliances such as refrigerators, washing machines, etc., child toys, reflective signage and other reflective articles on roads and clothing, sporting equipment such as snowboards, surfboards, skis, scooters, in-line skate wheels, scratch resistant CD's, stadium seats, aerospace reentry shields, plastic paper goods, sports helmets, plastic microwaveable cookware, and other applications for coating plastics and metal where a highly glossy and scratch resistant surface is desirable, while not being subject to algae or discoloration.

Invention copolymers are suitable for applications such as molded articles, including injection and blow molded bottles and molded items used in automotive articles, such as automotive interior and exterior trims. Examples of other methods and applications for making these polymers and for which these polymers may be useful are described in the Encyclopedia of Chemical Technology, by Kirk-Othmer, Fourth Edition, vol. 17, at pages 748–819. When the application is for molded articles, the molded articles may include a variety of molded parts, particularly molded parts related to and used in the automotive industry, such as for example bumpers, side panels, floor mats, dashboards and instrument panels. Foamed articles are another application and examples where foamed plastics, such as foamed polypropylene, are useful may be found in Encyclopedia of Chemical Technology, by Kirk-Othmer, Fourth Edition, vol. 11, at pages 730–783. Foamed articles are particularly useful for construction and automotive applications. Examples of construction applications include heat and sound insulation, industrial, and home appliances, and packaging. Examples of automotive applications include interior and exterior automotive parts, such as bumper guards, dashboards, and interior liners.

Invention polyolefin compositions are suitable for such articles as automotive components, wire and cable jacketing, pipes, agricultural films, geomembranes, toys, sporting equipment, medical devices, casting and blowing of packaging films, extrusion of tubing, pipes and profiles, sporting equipment, outdoor furniture (e.g., garden furniture) and playground equipment, boat and water craft components, and other such articles. In particular, the compositions are suitable for automotive components such as bumpers, grills, trim parts, dashboards and instrument panels, exterior door and hood components, spoiler, wind screen, hub caps, mirror housing, body panel, protective side molding, and other interior and external components associated with automobiles, trucks, boats, and other vehicles.

Other useful articles and goods may be formed economically by the practice of this invention include crates, containers, packaging, labware, such as roller bottles for culture growth and media bottles, office floor mats, instrumentation sample holders and sample windows; liquid storage containers such as bags, pouches, and bottles for storage and IV infusion of blood or solutions; packaging material including those for any medical device or drugs including unit-dose or other blister or bubble pack as well as for wrapping or containing food preserved by irradiation. Other useful items include medical tubing and valves for any medical device including infusion kits, catheters, and respiratory therapy, as well as packaging materials for medical devices or food which is irradiated including trays, as well as stored liquid, particularly water, milk, or juice, containers including unit servings and bulk storage containers as well as transfer means such as tubing, pipes, and such.

EXAMPLES

Synthesis of 4-allyl-2, 6-diisopropylaniline

4-Allyl-2, 6-diisoproylaniline was prepared from 2,6-diisoproylaniline according to the reference. The colorless liquid product was collected at 98.5° C./0.6 mmHg in 35% yield. $^1$H-NMR (400 MHz, CDCl$_3$): δ 6.85 (s, 2H, H—Ar), 5.98 (m, 1H, CH=C), 5.09 (d, 1H, C=C—H$_{trans}$), 5.03 (d, 1H, C=C—H$_{cis}$), 3.6 (br, 2H, NH$_2$), 3.30 (d, 2H, CH$_2$—C=C), 2.92 (m, 2H, CH(Me)$_2$), 1.26 (d, 12H, C(CH$_3$)$_2$).

Synthesis of bis(4-allyl-2,6-diisopropylphenylimino)acenaphthene (Ligand III)

A mixture of 1.00 g of acenaphthoquinone (5.5 mmol) and 4-allyl-2,6-diisopropylaniline (2.49 g, 11.1 mmol) in acetic acid (10 mL) was heated to reflux. After 1 h the mixture was cooled to room temperature, and the solid was filtered. The product was washed with acetic acid (5 mL), hexane (4×10 mL) and dried in vacuum, yielding 2.59 g as a yellow-golden solid (82%). $^1$H-NMR (400 MHz, CDCl$_3$): δ 7.86 (d, 2H, H$_o$-Ace-C=N), 7.37 (t, 2H, H$_m$-Ace-C=N), 7.07 (s, 4H, H—Ar—N=C), 6.65 (d, 2H, H$_p$-Ace-C=N), 6.15 (m, 2H, CH=C), 5.15 (m, 4H, C=C—H), 3.50 (d, 4H, CH$_2$—C=C), 3.00 (m, 4H, CH(Me)$_2$), 1.22 (d,12H, C(CH$_3$)$_2$), 0.96 (d, 12H, C(CH$_3$)$_2$). Anal. Calcd for C$_{42}$H$_{48}$N$_2$: C, 86.86; H, 8.32; N, 4.82. Found: C, 87.75; H, 7.35; N, 4.82.

Synthesis of [bis(4-allyl-2,6-diisopropylphenylimino)acenaphtheno]nickel(II) dibromide (Complex IV)

Ni(DME)Br$_2$ (77 mg, 0.25 mmol) and Ligand III (184 mg, 0.32 mmol) were combined in a Schlenk flask under a argon atmosphere. CH$_2$Cl$_2$ (20 mL) was added. And the reaction mixture was stirred at room temperature for 24 h. The solvent was removed in vacuum and the crude product washed three times with 10 mL of diethyl ether and dried in vacuum. The product was isolated as a dark-red powder (168 mg, 85% yield). Calcd for C$_{42}$H$_{48}$Br$_2$N$_2$Ni: C, 63.11; H, 6.05; N, 3.50. Found: C, 63.45; H, 5.60; N, 3.37.

In the presence of MMAO, the Ni (II) complexes can be used as ethylene polymerization catalysts.

Polymerization of Ethylene

The catalyst was weighed and added to a flame-dried Schlenk flask with a stirrer. The flask was back-filled three times with ethylene, and then charged with 50 ml of toluene. Stirring was begun, and after the equilibration of the solvent temperature, MMAO was added via syringe. The stirring was stopped, and the catalyst was transferred into the polymerization system. After 30 minutes, the polymerization was quenched with acidified ethanol, and the polymer was isolated by filtration and dried in vacuum at 40° C. for 10 hours.

Ethylene polymerization results[a]

| Run | Catalyst | Al/Ni | T (° C.) | Activity (× 10$^6$ gPEmol$^{-1}$Ni h$^{-1}$) | Mn[b] | Mw[b] | Mw/Mn[b] |
|---|---|---|---|---|---|---|---|
| 1 | Complex IV | 2500 | 25 | 2.67 | 110832 | 195796 | 1.767 |
| 2 | Complex IV | 2500 | 0 | 3.32 | 193660 | 478735 | 2.472 |
| 3 | Complex IV | 2500 | −15 | 2.83 | 221695 | 504193 | 2.274 |

[a]All of the pro-catalysts (1.0 μmol) activated with MMAO; ethylene polymerization time, 0.5 h; 50 mL of toluene; ethylene pressure: 0.1 MPa.
[b]Determined by GPC at 135° C.
[c]PC-4 is polymerized catalyst.
[d]4.0 μmol pro-catalyst PC-4; 0.4 MPa of ethylene pressure; polymerization time, 20 minutes without temperature control.
[e]3.26 μmol pro-catalyst SC-1(Shell-Core catalyst); 0.4 MPa of ethylene pressure; polymerization time, 15 minutes without temperature control.

Synthesis of Copolymer IV: Styrene and Complex IV

The copolymerizations of styrene with Complex IV at various ratios were carried out at 80±1° C. in toluene solution with AIBN in the ratio of 0.5% in argon atmosphere. In all processes, conversions were kept below 50%. The copolymers of styrene with Complex IV were obtained by removing toluene under vacuum, and then washing the polymer with a mixture of toluene (1 part) and hexane (4 parts) twice. The products were then reprecipitated from toluene into hexane and dried under vacuum. The copolymer compositions were determined by ICP elemental analysis.

Synthesis of SiO$_2$-Supported Copolymer (Core-Shell Catalyst VI): Styrene with Complex IV 5.0 g SiO$_2$ that had been dried under vacuum for 10 h, 5.0 g styrene, 0.5 g divinylbenzene and 50 ml of toluene were charged to a Schlenk bottle. The mixture was maintained at 70° C. for 30 min, and then 0.152 g Complex IV and initiator AIBN (0.5%) were added to the reaction system. The copolymerization was carried out at 80±1° C. in toluene under argon. The cross-linked copolymer of styrene with Complex IV was obtained by removing toluene under vacuum. The product was then washed with toluene and hexane. The copolymer composition was determined by ICP elemental analysis. Nickel content was 1.58 mg per 1 g core-shell catalyst.

In the presence of MMAO, the polymerized Ni (II) catalyst can be used as ethylene polymerization catalyst.

Polymerization of Ethylene

The catalyst was weighed out and added to a flame-dried Schlenk flask with a stirrer. The flask was back-filled three times with ethylene, and then charged with 50 ml of toluene. Stirring was begun, and after the equilibration of the solvent temperature, the MMAO was added via a syringe. The stirring was stopped, and the catalyst was transferred into the polymerization system. After 30 minutes, the polymerization was quenched with acidified ethanol, and the polymer was isolated by filtration and dried in vacuum at 40° C. for 10 hours.

| Entry | Pro-catalysts | T/°C. | Al/Ni (molar ratio) | Activity/10⁶ g (molNi)⁻¹ h⁻¹ | $M_n^b$ | $M_w^b$ | $M_w/M_n^b$ |
|---|---|---|---|---|---|---|---|
| 1 | PC-4c | 25 | 3500 | 1.80 | 129 703 | 263 814 | 2.034 |
| 2 |  | 0 | 3500 | 2.62 | 177 376 | 471 931 | 2.661 |
| 3 |  | −15 | 3500 | 1.50 | 207 424 | 444 792 | 2.144 |
| 4d |  | — | 3500 | 5.74 | n.d. | n.d. | n.d. |
| 5 | SC-1 | 25 | 3000 | 1.11 | 170 947 | 392 549 | 2.296 |
| 6 |  | 0 | 3000 | 0.86 | 178 239 | 433 879 | 2.434 |
| 7 |  | −15 | 3000 | 0.36 | 178 927 | 429 595 | 2.401 |
| 8e |  | — | 3000 | 6.92 | n.d. | n.d. | n.d. |

Results of ethylene polymerization results[a]

[a] All of the pro-catalysts (1.0 μmol) activated with MMAO; ethylene polymerization time, 0.5 h; 50 mL of toluene; ethylene pressure: 0.1 MPa.
[b] Determined by GPC at 135° C.
[c] PC-4 is polymerized catalyst.
[d] 4.0 μmol pro-catalyst PC-4; 0.4 MPa of ethylene pressure; polymerization time, 20 minutes without temperature control.
[e] 3.26 μmol pro-catalyst SC-1(Shell-Core catalyst); 0.4 MPa of ethylene pressure; polymerization time, 15 minutes without temperature control.

While certain representative embodiments and details have been shown to illustrate the invention, it will be apparent to skilled artisans that various process and product changes from those disclosed in this application may be made without departing from this invention's scope, which the appended claims define.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

What is claimed is:

1. A composition comprising the product of combining, in the presence of a free radical initiator, at least one olefin monomer, and a catalyst precursor compound wherein the catalyst precursor compound is represented by the formula:

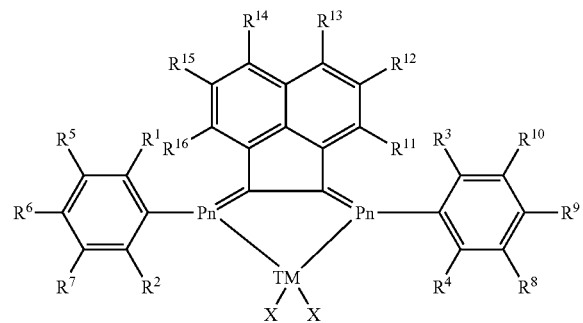

wherein
   (a) $R^1$–$R^{16}$ are hydrogen or hydrocarbyl radicals provided that at least one $R^5$–$R^{10}$ or $R^{11}$–$R^{16}$ is capable of polymerization by a free-radical-initiated polymerization reaction;
   (b) TM is a Group-9–11 transition metal, except Ni;
   (c) X represents an abstractable ligand; and
   (d) Pn represents nitrogen.

2. The composition of claim 1 wherein the catalyst precursor compound is represented by the formula:

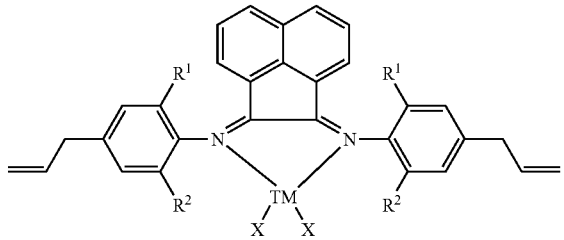

wherein
   (a) each X is independently selected from abstractable ligands;
   (b) $R^1$ and $R^2$ are independently hydrogen or hydrocarbyl groups; and
   (c) TM is a Group-9–11 metal, except Ni.

3. The composition of claim 2 wherein each $R^1$ and $R^2$ is independently selected from the group consisting of hydrogen and a $C_1$–$C_{50}$ hydrocarbyl group.

4. The composition of claim 3 wherein each $R^1$ and $R^2$ is independently selected from the group consisting of hydrogen and a $C_1$–$C_{30}$ hydrocarbyl group.

5. The composition of claim 4 wherein each $R^1$ and $R^2$ is independently selected from the group consisting of hydrogen and a $C_1$–$C_{10}$ hydrocarbyl group.

6. An olefin polymerization method comprising the step of contacting an olefin and the composition of claim 1 in the presence of a cocatalyst.

7. The composition of claim 1 wherein TM is Co.

8. The composition of claim 1 wherein the two abstractable ligands are hydride radicals; hydrocarbyl radicals; or hydrocarbyl-substituted, organometalloid radicals.

9. The composition of claim 8 wherein the two abstractable ligands join to form a 3-to-40-atom metallacycle ring.

10. The composition of claim 1, wherein the two abstractable ligands are halogen, alkoxide, aryloxide, amide, or phosphide radicals.

11. The composition of claim 1, wherein the two abstractable ligands are independently chloride, bromide, iodide, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hydride, phenyl, benzyl, phenethyl, tolyl methoxy, ethoxy, propoxy, butoxy, dimethylamino, diethylamino, methylethylamino, phenoxy, benzoxy, allyl, 1,1-dimethyl allyl, 2carboxymethyl allyl, acetylacetonate, 1,1,1,5,5,5-hexa-fluoroacetylacetonate, 1,1,1-trifluoro-acetylacetonate, or 1,1,1-trifluoro-5,5-di-methylacetylacetonate radicals.

12. The composition of claim 11 wherein at least one abstractable ligand is chloride or bromide.

13. A composition comprising the reaction product of the composition of claim 1 and an activator.

14. The composition of claim 13 wherein the activator is selected from the group consisting of alumoxanes, aluminum alkyls, alkyl aluminum halides, alkylaluminum alkoxides, discrete ionic activators, and Lewis acid activators.

15. The composition of claim 14 wherein the activator is methylalumoxane, modified methylalumoxane, ethylalumoxane, trimethyl aluminum, triethyl aluminum, triisopropyl aluminum, diethyl aluminum chloride, alkylaluminum alkoxides, ammonium borate salts, phosphonium borate salts, triphenyl carbenium borate salts, ammonium aluminate salts, phosphonium aluminate salts, triphenyl carbenium aluminate salts, trisarylborane acids, or polyhalogenated heteroborane anions.

16. The composition of claim 1 wherein the catalyst precursor compound is represented by the formulae:

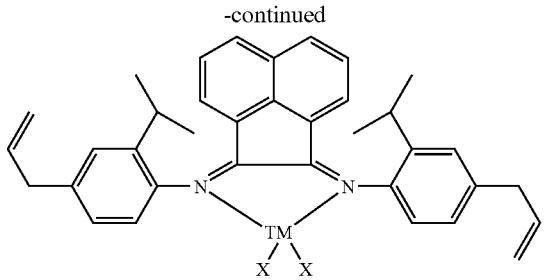
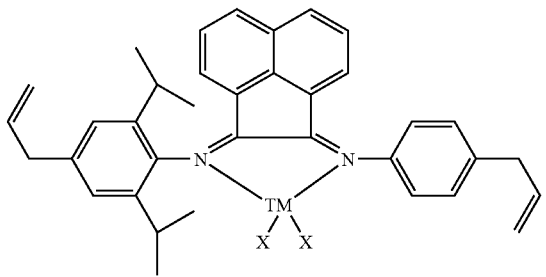
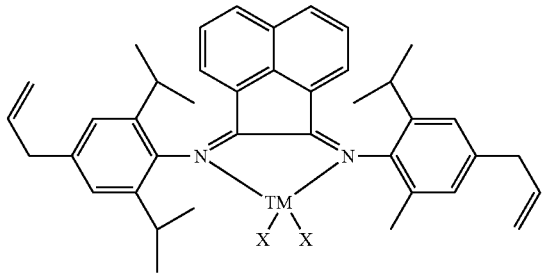
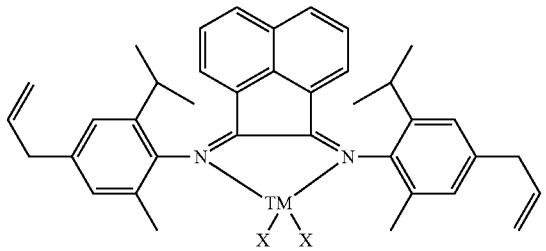
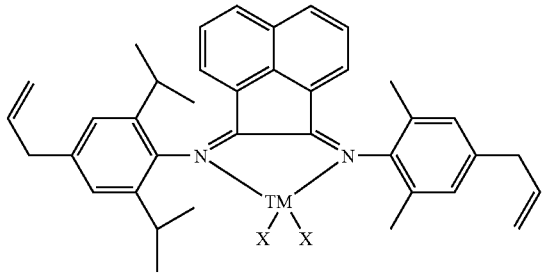
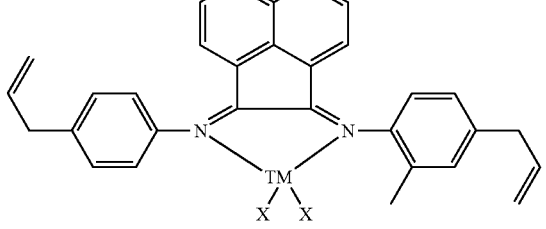
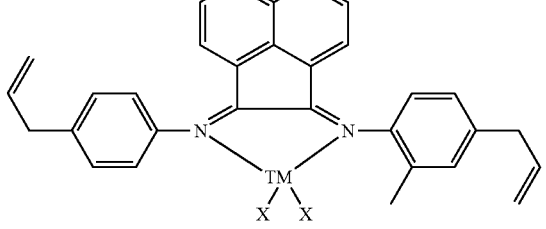
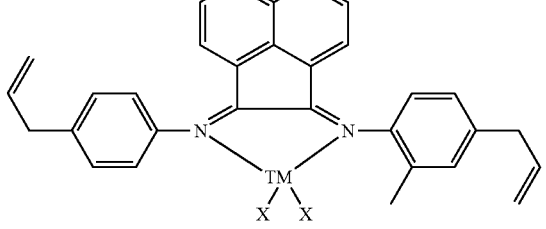
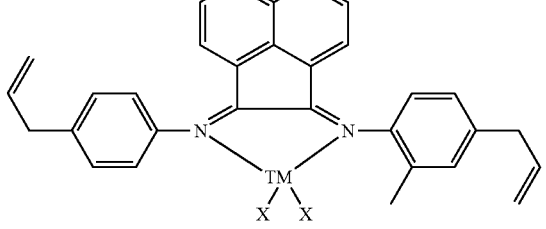
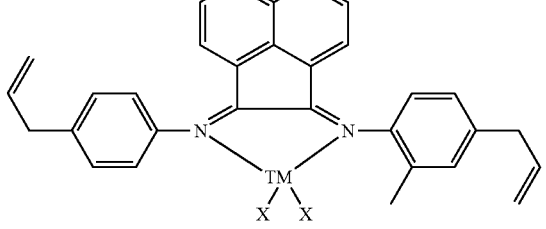
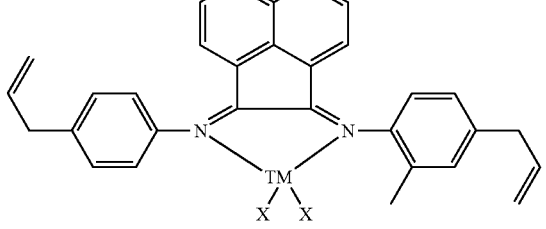
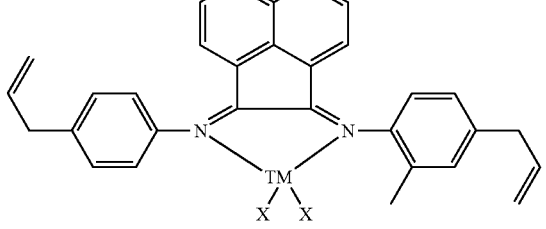
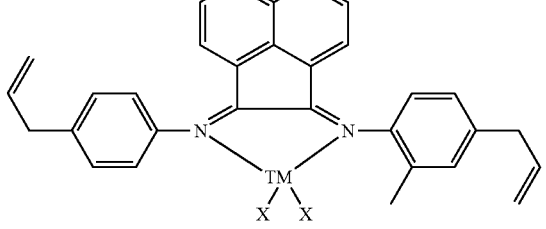

-continued
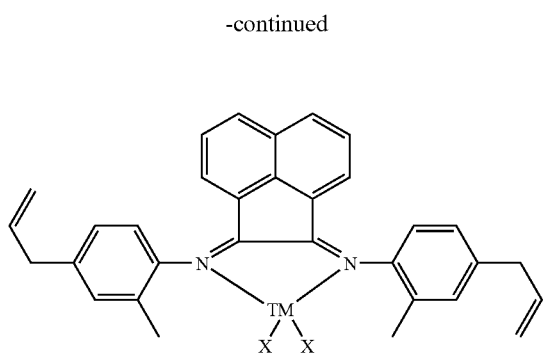
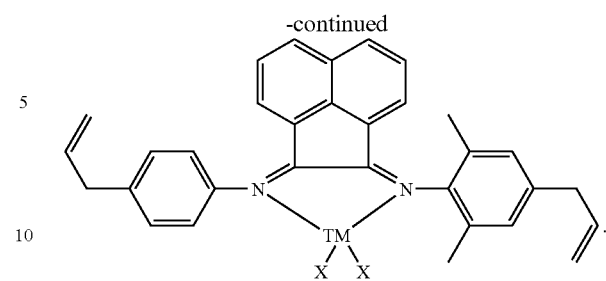
17. The composition of claim 16 wherein TM is Co.
* * * * *